US007192758B2

(12) United States Patent
Cahoon et al.

(10) Patent No.: US 7,192,758 B2
(45) Date of Patent: Mar. 20, 2007

(54) POLYNUCLEOTIDES ENCODING PHOSPHORIBOSYLANTHRANILATE ISOMERASE

(75) Inventors: Rebecca E. Cahoon, Webster Grove, MO (US); Steven Gutteridge, Wilmington, DE (US); Steven Vollmer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 429 days.

(21) Appl. No.: 10/295,220

(22) Filed: Nov. 15, 2002

(65) Prior Publication Data

US 2003/0129711 A1 Jul. 10, 2003

Related U.S. Application Data

(62) Division of application No. 09/647,224, filed as application No. PCT/US99/06582 on Mar. 22, 1999, now Pat. No. 6,482,631.

(60) Provisional application No. 60/079,386, filed on Mar. 26, 1998.

(51) Int. Cl.
*C12N 9/90* (2006.01)
*C12N 1/18* (2006.01)
*C12N 15/70* (2006.01)
*C12N 21/06* (2006.01)
*C07H 21/04* (2006.01)
*A01H 3/00* (2006.01)
*A01H 9/00* (2006.01)

(52) U.S. Cl. ............... 435/233; 435/69.1; 435/440; 435/419; 435/320.1; 435/252.3; 536/23.2; 800/278

(58) Field of Classification Search ............ 435/233, 435/325, 440; 800/278, 295
See application file for complete search history.

(56) References Cited

U.S. PATENT DOCUMENTS 6,476,212 B1 * 11/2002 Lalgudi et al. ............ 536/23.6

FOREIGN PATENT DOCUMENTS

WO    WO 97/26366 A1    7/1997
WO    WO 99/11800 A1    3/1999

OTHER PUBLICATIONS

Jiayang Li, Jiamin Zhao, Alan B. Rose, Renate Schmidt, and Robert L. Last, Arabidopsis Phosphoribosylanthranilate Isomerase: Molecular Genetic analysis of Triplicate Tryptophan Pathway, The Plant Cell, 7:p. 447, 1995.*
Alan B. Rose et al., Plant Phys., vol. 100:582-592, 1992. A phosphoribosylanthranilate Transferase Gene is defective in blue fluorescent *Arabdiopsis thaliana* tryptophan mutants.
Charles N. Hankins et al., Plant Phys., vol. 57(1):101-104, 1976, Some physical characteristics of the enzymes of l-tryptophan biosynthesis in higher plants.
Ikushugaku Zasshi—Japanes Journal Of Breeding, Tokyo, JP, vol. 46(2):28, 1996, Tozawa et al., isolation and analysis of gene coding for alpha-subunit of rice anthranilate synthase.
EMBL Sequence Library Database Accession No. Q9XJ29, Nov. 1, 1999, Tozawa, Y. et al., Rice cDNA encoding anthranilate synthase alpha subunit.
EMBL Sequence Library Database Accession No. T25248, Oct. 1, 1994, Shen, B. et al., Partial sequencing and mapping of clones from two maize cDNA libraries.
Bo Shen et al., Plant Mol. Biol., vol. 26:1085-1101, 1994, Partial sequencing and mapping of clones from two maize cDNA libraries.
Jorg Bohlmann et al., Plant J., vol. 7(3):491-501, 1995, Purification and cDNA cloning of anthranilate synthase from Ruta graveolens: modes of expression and properties of native and recombinant enzymes.
EMBL Sequence Library Database Accession No. M95067, Jun. 9, 1992, Keith, C.S. et al., Partial sequence analysis of 130 randomly selected maize cDNA clones.
Carlyn S. Keith et al., Plant Phys., vol. 101:329-332, 1993, Partial sequence analysis of 130 randomly selected maize cDNA clones.
Krishna K. Niyogi et al., Plant Cell, vol. 5:1011-1027, 1993, Suppressors of trp 1 Fluorescence Identify a New Arabidopsis Gene, TRP4, Encoding the Anthranilate Synthase beta subunit.
EMBL Sequence Library Database Accession No. T18773, May 14, 1994, Shen, B. et al., Partial sequencing and mapping of clones from two maize cDNa libraries.
EMBL Sequence Library Database Accession No. AA751371, Jan. 21, 1998, Nahm, B.H. et al. Large-scale sequencing analysis of ESTs from Rice Inmature Seed.
Elaine R. Radwanski et al., Mol. Gen. Genet., vol. 248:657-667, 1995, *Arabidopsis thaliana* tryptophan synthase alpha: gene cloning, expression, and subunit interaction.
Partial sequence analysis of 130 randomly selected maize cDNA clones.
EMBL Sequence Library Database Accession No. C27627, Aug. 6, 1997, Sasaki. T. et al., Rice cDNA from callus.
EMBL Sequence Library Database Accession No. AA660642, Nov. 14, 1997, Covitz, P.A. et al., Expressed sequence tags form a root hair-enriched Medicago truncatula library.
Derwent Publications Ltd., London, GB; Accession No. 99-228982. Hasegawa, H. et al., DNA encode first isoenzyme rice anthranilate synthetase improve tryptophan produce nutrient value crop rice maize wheat.
Vance C. Kramer et al., Plant Mol. Biol., vol. 27:1183-1188, 1995, Structure of a miaze tryptophan synthase alpha subunit gene with pith enhanced expression.

(Continued)

*Primary Examiner*—Rebecca E. Prouty
*Assistant Examiner*—Iqbal Chowdhury

(57) ABSTRACT

This invention relates to isolated nucleic acid fragments encoding phosphoribosylanthranilate isomerases, a tryptophan biosynthetic enzyme. The invention also relates to the construction of a chimeric gene comprising the nucleic acid fragment, in sense or antisense orientation, wherein expression of the chimeric gene results in production of altered levels of the phosphoribosylanthranilate isomerase in a transformed host cell.

12 Claims, 6 Drawing Sheets

OTHER PUBLICATIONS

Figure 1A:
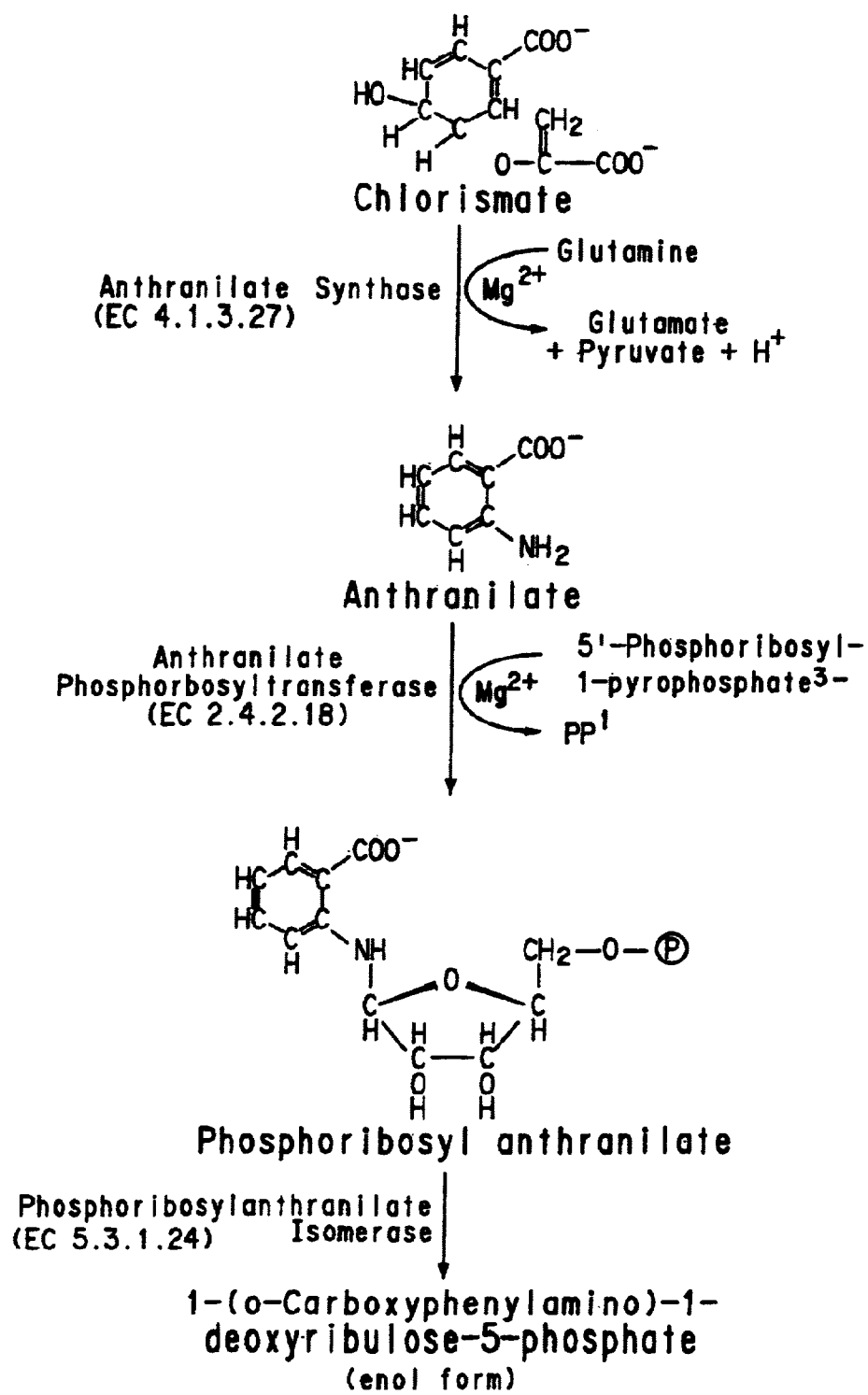

Veronique Blanc et al., Mol. Microbiol., vol. 23(2):191-202, 1997, Identification and analysis of genes from Streptomyces pristinaespiralis encoding enzymes involved in the biosynthesis of the 4-dimethylamino-L-phenylalanine precursor of pristinamycin 1.

Margaret S. Walker et al., Journ. of Biol. Chem., vol. 258(6):3571-2575, 1983, Purification and Characterization of the Trifunctional beta-subunit of Anthranilate Synthase from Neurospora crassa.

Krishna K. Niyogi et al., Plant Cell, vol. 4:721-733, 1992, Two anthranilate synthase genes in Arabidopsis: Defense-related regulation of the tryptophan pathway.

Jianmin Zhao et al., vol. 270:11):6081-6087, 1995, Immunological characterization and chloroplast localization of the tryptophan biosynthetic enzymes of the flowering plant *Arabidopsis thaliana*.

National Center for Biotechnology Information General Identifier No. 1575335, Mar. 7, 1997, Blanc, V. et al., Identification and analysis of genes from streptomyces pristineaespiralis encoding enzymes involved in the biosynthesis of the 4-dimethylamino-I-phenylalanine precursor of pristinamycin I.

National Center for Biotechnology Information General Identifier No. 1174783, May 30, 2000, Kramer, V.C. et al., Structure of a miaze tryptophan synthase alpha subunit gene with pith enhanced expression.

National Center for Biotechnology Information General Identifier No. 960289, Aug. 26, 1995, Bohlmann, J. et al., Purification and cDNA cloning of anthranilate synthase from Ruta graveolens: modes of expression and properties of native and recombinant enzymes.

National Center for Biotechnology Information General Identifier No. 541849, Jun. 22, 1999, Niyogi, K.K. et al., Suppressors of trp1 fluorescence identify a new arabidopsis gene, TRP4, encoding the anthranilate synthase beta subunit.

National Center for Biotechnology Information General Identifier No. 2129755, May 19, 2000, Radwanski, E.R. et al., *Arabidopsis thaliana* tryptophan synthase alpha: gene cloning, expression, and subunit interaction.

Reinhard Sterner et al., $(\beta\alpha)_8$—barrel proteins of trytophan biosynthesis in the hyperthermophile Thermotoga maritima, The EMBO Journal, vol. 14, No. 18, pp. 4395-4402, 1995.

Jiayang Li et al., Arabidopsis Phosphoribosylanthranilate Isomerase: Molecular Genetic Analysis of Triplicate Tryptophan Pathway Genes, The Plant Cell, vol. 7, pp. 447-461, Apr. 1995.

Michael Hennig et al., Crystal Structure at 2.0 A Resolution of Phosphoribosyl Anthranilate Isomerase from the Hyperthermophile *Thermotoga maritime:* Possible Determinants of Protein Stability, Biochemistry, vol. 36:6009-6016, 1997.

Jorg Eder et al., Protein Engineering of a Disulfide Bond in a $\beta/\alpha$—Barrel Protein, Biochemistry, vol. 31:4437-4444, 1992.

Matthias Wilmanns et al., Three-dimensional Structure of the Bifunctional Enzyme Phosphoribosylanthranilate Isomerase: Indoleglycerolphosphate Synthase from *Escherichia coli* Refined at 20 A Resolution, J. Mol. Biol., vol. 223:477-507, 1992.

* cited by examiner

```
SEQ ID NO:25   MD--------------------RKINFRAPSQF-----SIRAQQSDLKESLAVS
SEQ ID NO:10   MESLLASRSIRSSFSAVA-STRGAASPRPSRVA-------TLASAGAGARSRALR
SEQ ID NO:14   MEGLA---SLKAPFPATPFLSSRPTSILPSQ-ASFRKRSSFLSFSVHAQVESDDGSAVV
                                                                         60

SEQ ID NO:25   SSSVEDKGNVLRIKEWEVEMYQEELAISQGIRIRRKPPSKAPLGYSGPFELRLHNNDADS
SEQ ID NO:10   AGHTDDMLNAKELVQWENGLSFNDIAARQGIRIRRHCRPTASL------KEIEEELGA
SEQ ID NO:14   ATSGESVTEVLKIKEWEVGMFQNEVAASQGIRIRRPPSGPPLHYVGPFQFRLQN-EGNT
                                                                          120

SEQ ID NO:25   PRNILEEITWYKDVEVSRMKELNPLDVLKKAVEDAPPTRDFVGALRMAHKRPGFPGLIAE
SEQ ID NO:10   PLNILEKIIWDKEIEVAEGHAKKPLEEVIQAATKAPPSRDFYGALEAAYKRNGVPALIAE
SEQ ID NO:14   PRNILEEIVWNKDTEVSQLKERKPLGVLKKALENAPPARDFIGALKAANERTGLPGLIAE
                                                                          180

SEQ ID NO:25   VKKASPSRGILKENFDPVEIAQAYEKGGAACLSVLTDQKYFQGGFENLEAIRSAGVKCPL
SEQ ID NO:10   VKKASPSRGVLRENFNPVEIAQAYEKNGAACLSILTDEKYFQGSFDNLEKVRSSXVKCPL
SEQ ID NO:14   VKKASPSRGILREDFDPVEIAKAYEKGGAACLSVLTDEKYFKGSFENLEAIRKAGIKCPL
                                                                          240
```

FIG. 2A

```
                 *****  *    *   **    *  ** ***********  **  *** *********  ** * ********
SEQ ID NO:25     LCKEFVVDPWQIYYARTKGADAVLLIAAVLADLEITFLLKICKKLSLAALVEVHDEREMG
SEQ ID NO:10     LCKEFVIDKWQIYNARSKGADAILLIAAVLPDLDIRKFLQICEELGMTALIEVHDEREME
SEQ ID NO:14     LCKEFIIDAWQLYYARTKGADAVLLIAAVLPDLDIKYMIKICKLLGLTALVEVHDEREFD
                 241                                                          300

*** *  *  *****   ****  **   **  **                  *   ********* ***
SEQ ID NO:25     RVLGIEGIELVGINNRSLETFEVDISNTKKLLALEGEHGRQIRERDMIVVGESGLFTPDD
SEQ ID NO:10     RVLKINGVKLIGINNRSLETFVVDTSNTKMLLE---KHGDIIREKGILVVGESGLFTPDD
SEQ ID NO:14     RVLAIEGIELIGINNRNLETFELDISITKKLL---EGERGKIIHERGIIMVGESGLFTPDD
                 301                                                          360

**** * *  ***** ****   *   *    *    *  *    *** 
SEQ ID NO:25     IAYVQAAGVKAVLVGESIVKQNDPEKGIAGLFGRNISHT.
SEQ ID NO:10     VAYVQNAGVSAVLVGESLVKQECPGRAIVGLFGKELLH-
SEQ ID NO:14     IAYVQEAGVKAILVGESIVKQSDPGKGISNLFGKDISLG.
                 361                                  400
```

FIG. 2B

```
SEQ ID NO:26   MSTGISSDLHLHPRALNFSKTSKSGLSN.RKVSFSSVGYAQNRKLSCSVSSTENVAPKDD
SEQ ID NO:20   MLLASSTR-----RYEQFPLARNNGLPRFSRVKMSCLGTNQSNHHSDTVRSS---SPSCG
SEQ ID NO:24   MATAFSTK------QPLRVATPTNKWRPRLPLIKMQY---SSNKRASASISLP---SSAEG
                1                                                          60
                *            *  *********  *  ***   ***  *  * * *  **

SEQ ID NO:26   DRGKDRPLVKMCGITSARDAAMAVEAGADFIGMIIWPHSKRSISLSVAKDISQVAREGGA
SEQ ID NO:20   DTRKVHPVVKMCGITSARDAEMAVKAGAELIGMILWPNSKRSVSLLEAKEISRVVQSYGA
SEQ ID NO:24   VERN.EPIVKMCGITSARDAEFAAKAGAKLIGMILWPKSKRSVQRSEAKEISRVAKSYGA
                61                                                         120
                    ********** ***  **  ***  ****  ** ***** * ** *** *   **

SEQ ID NO:26   KPVGVFVEDDENTILRAADSSDLELVQLHGNSSRAAFSRLVRERKVIYVLNANEDGKLLN
SEQ ID NO:20   ESVGVFVEDDNEETILRVSDSCDLNFVQLHGDESRALVHTLSKNNRIVYVLNADDDGKLIN
SEQ ID NO:24   EAVGVFVDDDEETILRVADSCNLQLIQLHGDSSRALVPALAKNNRIVYVLNADADGKLIN
                121                                                        180
                  ***** * * **** *** * *  **** * **    * *** *****   ***

SEQ ID NO:26   VVPEEDGHLADWILVDSATGGSGKGFNWAQFKLPSVRSRNGWLLAGGINPTNVSEALSIL
SEQ ID NO:20   IPDIE.YEL.DWYLVDSAKGGSGKGFNWQKFQMPSVKSKNGWLLAGGLHADNVCEAFSAL
SEQ ID NO:24   SPPSEEYDI.DWFLVDSAEGGSGKGFNWDNFRMPSVKSKNGWLLAGGLHADNVCQAASAL
                181                                                        240
                   *    *  ***** **********    ***  ********    * *  * **
```

FIG. 3A

```
                      * * ******* *** ** * ** * *
SEQ ID NO:26          QPDGIDVSSGICGIDGIQKDKSKISSFITAVRSVH------Y..........
SEQ ID NO:20          KPDGVDVSSGICGRDGIRKDADRINSFISNVKSLN------FLS........
SEQ ID NO:24          KPNGVDVSSGICSPDGISKDPKRISSFMRSVQSLSSRRGLYLDAPGLL.
                      241                                             289
```

FIG. 3B

POLYNUCLEOTIDES ENCODING PHOSPHORIBOSYLANTHRANILATE ISOMERASE

This application is a divisional of U.S. application Ser. No. 09/647,224, filed Jul. 16, 2001, now U.S. Pat. No. 6,482,631, which is the National Stage Application, according to 35 U.S.C. 371, of International Application No. PCT/US99/06582, filed Mar. 22, 1999, which claims the benefit of U.S. Provisional Application No. 60/079,386, filed Mar. 26, 1998.

FIELD OF THE INVENTION

This invention is in the field of plant molecular biology. More specifically, this invention pertains to nucleic acid fragments encoding enzymes involved in tryptophan biosynthesis in plants and seeds.

BACKGROUND OF THE INVENTION

Many vertebrates, including man, lack the ability to manufacture a number of amino acids and therefore require these amino acids preformed in their diet. These are called essential amino acids. Plants are able to synthesize all twenty amino acids and serve as the ultimate source of the essential amino acids for humans and animals. Thus, the ability to manipulate the production and accumulation of the essential amino acids in plants is of considerable importance and value. Furthermore, the inability of animals to synthesize these amino acids provides a useful distinction between animal and plant cellular metabolism. This can be exploited for the discovery of herbicidal chemical compounds that target enzymes in the plant biosynthetic pathways of the essential amino acids and thus have low toxicity to animals.

Tryptophan is an essential amino acid. In plants, the biosynthesis of tryptophan from chorismic acid (see FIGS. 1A and 1B) requires five enzymatic steps catalyzed by anthranilate synthase (EC 4.1.3.27), anthranilate phosphoribosyl-transferase (EC 2.4.2.18), phosphoribosylanthranilate isomerase (EC 5.3.1.24), indole-3-glycerol phosphate synthase (EC 4.1.1.48) and tryptophan synthase (EC 4.2.1.20). The tryptophan pathway leads to the biosynthesis of many secondary metabolites including the hormone indole-3-acetic acid, antimicrobial phytoalexins, alkaloids and glucosinolates. Anthranilate phosphoribosyl-transferase is encoded by the PAT1 locus in *Arabidopsis thaliana* and the trpD locus in bacteria. Anthranilate phosphoribosyltransferase catalyzes the second step in tryptophan biosynthesis from chorismate forming 5-phosphoribosylanthranilate from anthranilate. *Arabidopsis* mutants in this gene are blue fluorescent under UV light due to accumulation of anthranilate compounds. Analysis of *Arabidopsis* plants expressing translational fusions of betaglucuronidase and different sections of the PAT1 gene indicates that the entire plastid transit peptide and the first two introns of PAT 1 are required for efficient transcription and translation (Rose, A. B. and Last, R. L. (1997) *Plant J* 11:455–464). Anthranilate phosphoribosyltransferase purifies from *Saccharomyces cerevisiae* as a dimer (Hommel, U. et al. (1989) *Eur J Biochem* 180:33–40).

Phosphoribosylanthranilate isomerase catalyzes the third step in tryptophan biosynthesis from chorismate forming 1-(O-carboxyphenylamino)-1-deoxyribulose-5-phosphate. Three nonallelic genes encode phosphoribosylanthranilate isomerase in *Arabidopsis thaliana*. All three alleles contain a plastid transit peptide at their N-terminus, are over 90% identical and are flanked by nearly identical 350 nucleotide repeats (Li, J. Y. et al. (1995) *Plant Cell* 7:47–461).

Indole-3-glycerol phosphate synthase catalyzes the fifth step in tryptophan biosynthesis from chorismate producing indole-glycerol phosphate from 1-(2-carboxyphenylamino)-1-deoxyribulose 5'-phosphate. Mutation of seven invariant polar residues in the active site of the enzyme from *Escherichia coli* have allowed the identification of catalytically essential residues. Random saturation mutagenesis indicates that K114, E163, E53 and N184 are located in the active site of the enzyme (Darimont, B. et al. (1998) *Protein Sci* 7:1221–1232).

Few of the genes encoding enzymes from the tryptophan pathway in corn, soybeans, rice and wheat, have been isolated and sequenced. For example, no corn, soybean, rice or wheat genes have been reported for anthranilate phosphoribosyltransferase, phosphoribosylanthranilate isomerase or indole-3-glycerol phosphate synthase. Accordingly, the availability of nucleic acid sequences encoding all or a portion of these enzymes would facilitate studies to better understand cellular biosynthetic pathways, provide genetic tools for the manipulation of those pathways, provide a means to evaluate chemical compounds for their ability to inhibit the activity of enzymes in the tryptophan biosynthetic pathway.

SUMMARY OF THE INVENTION

The instant invention relates to isolated nucleic acid fragments encoding tryptophan biosynthetic enzymes. Specifically, this invention concerns an isolated nucleic acid fragment encoding an anthranilate phosphoribosiltransferase, an indole-3-glycerol phosphate synthase or a phosphoribosylanthranilate isomerase. In addition, this invention relates to a nucleic acid fragment that is complementary to the nucleic acid fragment encoding anthranilate phosphoribosiltransferase, indole-3-glycerol phosphate synthase or phosphoribosylanthranilate isomerase.

An additional embodiment of the instant invention pertains to a polypeptide encoding all or a substantial portion of a tryptophan biosynthetic enzyme selected from the group consisting of anthranilate phosphoribosiltransferase, indole-3-glycerol phosphate synthase and phosphoribosylanthranilate isomerase.

In another embodiment, the instant invention relates to a chimeric gene encoding an anthranilate phosphoribosiltransferase, an indole-3-glycerol phosphate synthase or a phosphoribosylanthranilate isomerase, or to a chimeric gene that comprises a nucleic acid fragment that is complementary to a nucleic acid fragment encoding an anthranilate phosphoribosiltransferase, an indole-3-glycerol phosphate synthase or a phosphoribosylanthranilate isomerase, operably linked to suitable regulatory sequences, wherein expression of the chimeric gene results in production of levels of the encoded protein in a transformed host cell that is altered (i.e., increased or decreased) from the level produced in an untransferred host cell.

In a further embodiment, the instant invention concerns a transformed host cell comprising in its genome a chimeric gene encoding an anthranilate phosphoribosiltransferase, an indole-3-glycerol phosphate synthase or a phosphoribosylanthranilate isomerase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an anthranilate phosphoribosiltransferase, an indole-3-glycerol phosphate synthase or a phosphoribosylanthranilate isomerase in a transformed host cell comprising: a) transforming a host cell with a chimeric gene comprising a nucleic acid fragment encoding an anthranilate phosphoribosil-transferase, an indole-3-glycerol phosphate synthase or a phosphoribosyl-anthranilate isomerase; and b) growing the transformed host cell under conditions that are suitable for expression of the chimeric gene wherein expression of the chimeric gene results in production of altered levels of anthranilate phosphoribosiltransferase, indole-3-glycerol phosphate synthase or phosphoribosyl-anthranilate isomerase in the transformed host cell.

An addition embodiment of the instant invention concerns a method for obtaining a nucleic acid fragment encoding all or a substantial portion of an amino acid sequence encoding an anthranilate phosphoribosiltransferase, an indole-3-glycerol phosphate synthase or a phosphoribosylanthranilate isomerase.

A further embodiment of the instant invention is a method for evaluating at least one compound for its ability to inhibit the activity of an anthranilate phosphoribosiltransferase, an indole-3-glycerol phosphate synthase or a phosphoribosylanthranilate isomerase, the method comprising the steps of: (a) transforming a host cell with a chimeric gene comprising a nucleic acid fragment encoding an anthranilate phosphoribosiltransferase, an indole-3-glycerol phosphate synthase or a phosphoribosylanthranilate isomerase, operably linked to suitable regulatory sequences; (b) growing the transformed host cell under conditions that are suitable for expression of the chimeric gene wherein expression of the chimeric gene results in production of anthranilate phosphoribosiltransferase, indole-3-glycerol phosphate synthase or phosphoribosylanthranilate isomerase in the transformed host cell; (c) optionally purifying the anthranilate phosphoribosiltransferase, the indole-3-glycerol phosphate synthase or the phosphoribosylanthranilate isomerase expressed by the transformed host cell; (d) treating the anthranilate phosphoribosiltransferase, the indole-3-glycerol phosphate synthase or the phosphoribosylanthranilate isomerase with a compound to be tested; and (e) comparing the activity of the anthranilate phosphoribosiltransferase, the indole-3-glycerol phosphate synthase or the phosphoribosylanthranilate isomerase that has been treated with a test compound to the activity of an untreated anthranilate phosphoribosiltransferase, indole-3-glycerol phosphate synthase or phosphoribosyl-anthranilate isomerase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

Figure 1B:
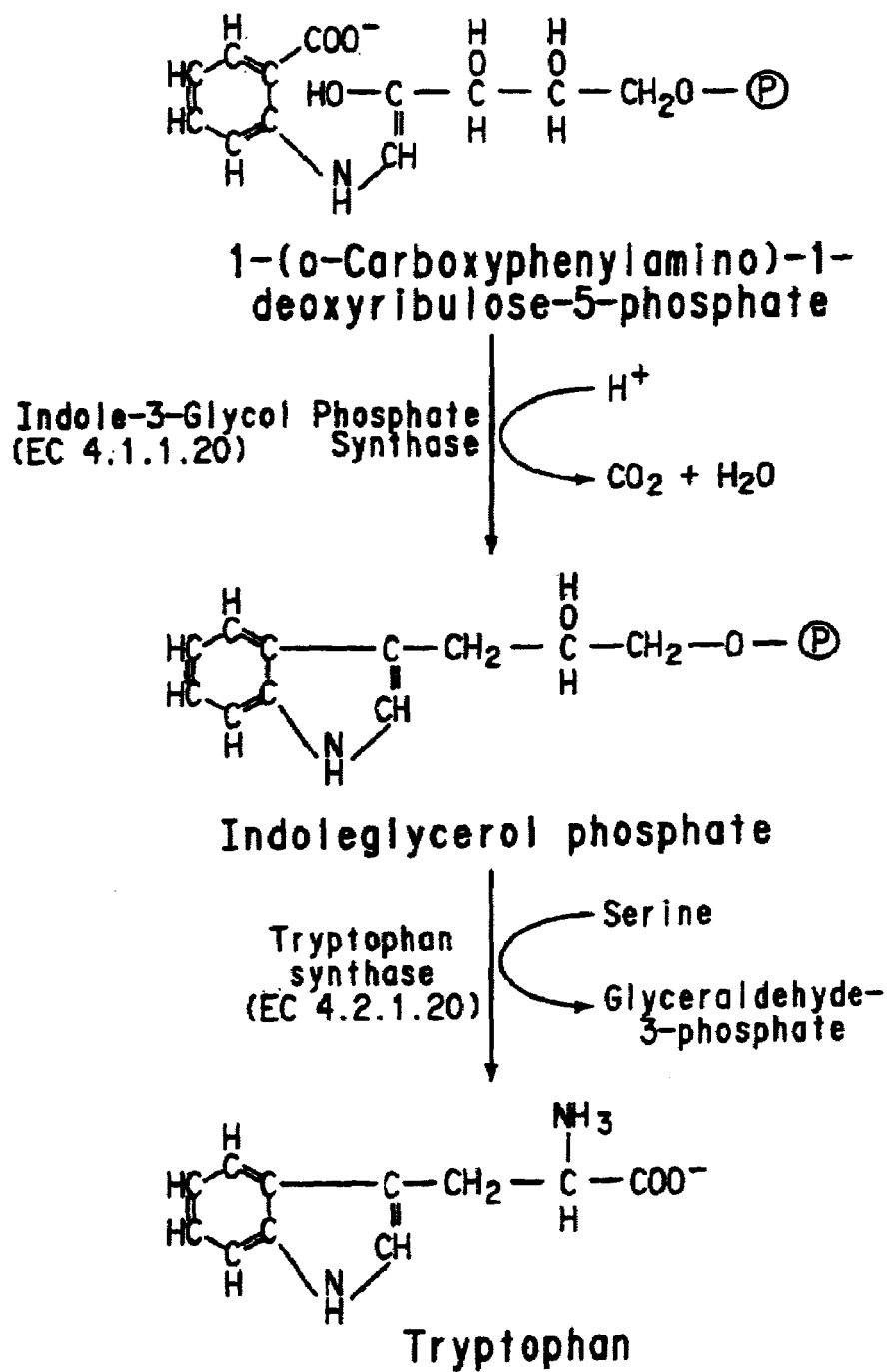

FIGS. 1A and 1B depicts biochemical pathway for the production of tryptophan from chorismate.

FIGS. 2A and 2B shows an alignment of the amino acid sequences from *Arabidopsis thaliana* indole-3-glycerol phosphate synthase (SEQ ID NO:25), the instant corn indole-3-glycerol phosphate synthase (contig of p0128.cpicq73r, p0041.crtav17rb, p0002.cgevb40r, p0091.cmarc86r, cr1n.pk0121.b7 and chp2.pk0003.c4; SEQ ID NO:10) and the instant soybean indole-3-glycerol phosphate synthase (sdp2c.pk001.f3; SEQ ID NO:14). Amino acid which are identical among all sequences are indicated with an asterisk (*) above the alignment. Dashes are used by the program to maximize alignment of the sequences.

FIGS. 3A and 3B shows an alignment of the amino acid sequences from *Arabidopsis thaliana* phosphoribosylanthranilate sisomerase (SEQ ID NO:26), the instant corn phosphoribosylanthranilate isomerase (ceb1.pk0026.d2; SEQ ID NO:20) and the instant wheat phosphoribosylanthranilate isomerase (wr1.pk0127.e10; SEQ ID NO:24). Amino acid which are identical among all sequences are indicated with an asterisk (*) above the alignment. Dashes are used by the program to maximize alignment of the sequences.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the contig assembled from a portion of the cDNA insert in clones p0037.crwan82r, p0022.cglne15r, cbn10.pk0045.b8, p0109.cdadc66r, cr1n.pk0145.g6, cco1.pk0002.f11, cs1.pk0056.d10, p0103.ciaag55r and p0104.cabbg36r encoding an entire corn anthranilate phosphoribosyltransferase.

SEQ ID NO:2 is the deduced amino acid sequence of an entire corn anthranilate phosphoribosyltransferase derived from the nucleotide sequence of SEQ ID NO:1.

SEQ ID NO:3 is the nucleotide sequence comprising the entire cDNA insert in clone ssm.pk0059.f8 encoding the C-terminal half of a soybean anthranilate phosphoribosyltransferase.

SEQ ID NO:4 is the deduced amino acid sequence of the C-terminal half of a soybean anthranilate phosphoribosyltransferase derived from the nucleotide sequence of SEQ ID NO:3.

SEQ ID NO:5 is the nucleotide sequence comprising the entire cDNA insert in clone wre1.pk0003.b12 encoding the C-terminal half of a wheat anthranilate phosphoribosyltransferase.

SEQ ID NO:6 is the deduced amino acid sequence of the C-terminal half of a wheat anthranilate phosphoribosyltransferase derived from the nucleotide sequence of SEQ ID NO:5.

SEQ ID NO:7 is the nucleotide sequence comprising the entire cDNA insert in clone cen3n.pk0147.h5 encoding a substantial portion of a corn indole-3-glycerol phosphate synthase.

SEQ ID NO:8 is the deduced amino acid sequence of a substantial portion of a corn indole-3-glycerol phosphate synthase derived from the nucleotide sequence of SEQ ID NO:7.

SEQ ID NO:9 is the nucleotide sequence comprising the contig assembled from the cDNA insert in clones p0128.cpicq73r, p0041.crtav17rb, p0002.cgevb40r, p0091.cmarc86r and the entire cDNA insert in clones cr1n.pk0121.b7 and chp2.pk0003.c4 encoding an entire corn indole-3-glycerol phosphate synthase.

SEQ ID NO:10 is the deduced amino acid sequence of an entire corn indole-3-glycerol phosphate synthase derived from the nucleotide sequence of SEQ ID NO:9.

SEQ ID NO:11 is the nucleotide sequence comprising the entire cDNA insert in clone r10n.pk0021.f11 encoding a portion of a rice indole-3-glycerol phosphate synthase.

SEQ ID NO:12 is the deduced amino acid sequence of a portion of a rice indole-3-glycerol phosphate synthase derived from the nucleotide sequence of SEQ ID NO:11.

SEQ ID NO:13 is the nucleotide sequence comprising the entire cDNA insert in clone sdp2c.pk001.f3 encoding an entire soybean indole-3-glycerol phosphate synthase.

SEQ ID NO:14 is the deduced amino acid sequence of an entire soybean indole-3-glycerol phosphate synthase derived from the nucleotide sequence of SEQ ID NO:13.

SEQ ID NO:15 is the nucleotide sequence comprising the entire cDNA insert in clone wre1n.pk0075.b10 encoding a substantial portion of a wheat indole-3-glycerol phosphate synthase.

SEQ ID NO:16 is the deduced amino acid sequence of a substantial portion of a wheat indole-3-glycerol phosphate synthase derived from the nucleotide sequence of SEQ ID NO:15.

SEQ ID NO:17 is the nucleotide sequence comprising the contig assembled from a portion of the cDNA insert in clones cco1n.pk0030.b11, p0068.clsaa67r and p0099.ctbai70r encoding the N-terminal half of a corn phosphoribosylanthranilate isomerase.

SEQ ID NO:18 is the deduced amino acid sequence of the N-terminal half of a corn phosphoribosylanthranilate isomerase derived from the nucleotide sequence of SEQ ID NO:17.

SEQ ID NO:19 is the nucleotide sequence comprising the entire cDNA insert in clone ceb1.pk0026.d2 encoding an entire corn phosphoribosylanthranilate isomerase.

SEQ ID NO:20 is the deduced amino acid sequence of an entire corn phosphoribosylanthranilate isomerase derived from the nucleotide sequence of SEQ ID NO:19.

SEQ ID NO:21 is the nucleotide sequence comprising a portion of the cDNA insert in clone rsr9n.pk001.g2 encoding the C-terminal half of a rice phosphoribosylanthranilate isomerase.

SEQ ID NO:22 is the deduced amino acid sequence of the C-terminal half of a rice phosphoribosylanthranilate isomerase derived from the nucleotide sequence of SEQ ID NO:21.

SEQ ID NO:23 is the nucleotide sequence comprising the entire cDNA insert in clone wr1.pk0127.e10 encoding an entire wheat phosphoribosyl-anthranilate isomerase.

SEQ ID NO:24 is the deduced amino acid sequence of an entire wheat phosphoribosylanthranilate isomerase derived from the nucleotide sequence of SEQ ID NO:23.

SEQ ID NO:25 is the amino acid sequence of an *Arabidopsis thaliana* indole-3-glycerol phosphate synthase having an NCBI General Identifier No. 1351303.

SEQ ID NO:26 is the amino acid sequence of a *Arabidopsis thaliana* phosphoribosylanthranilate isomerase having an NCBI General Identifier No. 619749.

SEQ ID NO:27 is the nucleotide sequence of the PCR primer pIGSs-F1.

SEQ ID NO:28 is the nucleotide sequence of the PCR primer pIGSs-F2.

SEQ ID NO:29 is the nucleotide sequence of the PCR primer pIGSs-M1.

SEQ ID NO:30 is the nucleotide sequence of the PCR primer pIGSs-M2.

SEQ ID NO:31 is the nucleotide sequence of the PCR primer pSK-B1.

SEQ ID NO:32 is the nucleotide sequence of the PCR primer pSK-B2.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are greater than 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence often or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the anthranilate phosphoribosiltransferase, the indole-3-glycerol phosphate synthase or the phosphoribosylanthranilate isomerase proteins as set forth in SEQ ID NOs:2, 4, 6, 8, 10, 12, 14, 16, 18, 20, 22 and 24. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several tryptophan biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Tryptophan Biosynthetic Enzymes

| Enzyme | Clone | Plant |
|---|---|---|
| Anthranilate phosphoribosyltransferase | Contig of: | Corn |
| | p0037.crwan82r | |
| | p0022.cglne15r | |
| | cbn10.pk0045.b8 | |
| | p0109.cdadc66r | |
| | cr1n.pk0145.g6 | |
| | cco1.pk0002.f11 | |
| | cs1.pk0056.d10 | |
| | p0103.ciaag55r | |
| | p0104.cabbg36r | |
| | ssm.pk0059.f8 | Soybean |
| | wre1.pk0003.b12 | Wheat |
| Indole-3-glycerol phosphate synthase | cen3n.pk0147.h5 | Corn |
| | Contig of: | Corn |
| | p0128.cpicq73r | |
| | p0041.crtav17rb | |
| | p0002.cgevb40r | |
| | p0091.cmarc86r | |
| | cr1n.pk0121.b7 | |
| | chp2.pk0003.c4 | |
| | rl0n.pk0021.f11 | Rice |
| | sdp2c.pk001.f3 | Soybean |
| | wre1n.pk0075.b10 | Wheat |
| Phosphoribosylanthranilate isomerase | Contig of: | Corn |
| | cco1n.pk0030.b11 | |
| | p0068.clsaa67r | |
| | p0099.ctbai70r | |
| | ceb1.pk0026.d2 | Corn |
| | rsr9n.pk001.g2 | Rice |
| | wr1.pk0127.e10 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other anthranilate phosphoribosiltransferases, indole-3-glycerol phosphate synthases or phosphoribosylanthranilate isomerases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *Proc. Natl. Acad. Sci. USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed anthranilate phosphoribosiltransferase, indole-3-glycerol phosphate synthase or phosphoribosylanthranilate isomerase are present at higher or lower levels than normal or in cell types or developmental stages in which they are not normally found. This would have the effect of altering the level of tryptophan biosynthesis in those cells. Overexpression of any one of these three enzymes should lead to the production of plants with higher levels of tryptophan, an essential amino acid. These enzymes catalyze a pathway not found in humans of higher animals making them ideal candidates for the discovery of herbicides.

Overexpression of the anthranilate phosphoribosiltransferase, the indole-3-glycerol phosphate synthase or the phosphoribosylanthranilate isomerase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant tryptophan biosynthetic enzyme to different cellular compartments, or to facilitate its secretion from the cell. It is thus envisioned that the chimeric gene described above may be further supplemented by altering the coding sequence to encode anthranilate phosphoribosiltransferase, indole-3-glycerol phosphate synthase or phosphoribosylanthranilate isomerase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100: 1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding anthranilate phosphoribosiltransferase, indole-3-glycerol phosphate synthase or phosphoribosylanthranilate isomerase in plants for some applications. In order to accomplish this, a chimeric gene designed for co-suppression of the instant tryptophan biosynthetic enzyme can be constructed by linking a gene or gene fragment encoding an anthranilate phosphoribosiltransferase, an indole-3-glycerol phosphate synthase or a phosphoribosylanthranilate isomerase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant anthranilate phosphoribosiltransferase, indole-3-glycerol phosphate synthase or phosphoribosylanthranilate isomerase (or portions thereof) may be produced in heterologous host cells, particularly in the cells of microbial hosts, and can be used to prepare antibodies to the these proteins by methods well known to those skilled in the art. The antibodies are useful for detecting anthranilate phosphoribosiltransferase, indole-3-glycerol phosphate synthase or phosphoribosylanthranilate isomerase in situ in cells or in vitro in cell extracts. Preferred heterologous host cells for production of the instant anthranilate phosphoribosiltransferase, indole-3-glycerol phosphate synthase or phosphoribosylanthranilate isomerase are microbial hosts. Microbial expression systems and expression vectors containing regulatory sequences that direct high level expression of foreign proteins are well known to those skilled in the art. Any of these could be used to construct a chimeric gene for production of the instant anthranilate phosphoribosiltransferase, indole-3-glycerol phosphate synthase or phosphoribosylanthranilate isomerase. This chimeric gene could then be introduced into appropriate microorganisms via transformation to provide high level expression of the encoded tryptophan biosynthetic enzyme. An example of a vector for high level expression of the instant anthranilate phosphoribosiltransferase, indole-3-glycerol phosphate synthase or phosphoribosylanthranilate isomerase in a bacterial host is provided (Example 9).

Additionally, the instant anthranilate phosphoribosiltransferase, indole-3-glycerol phosphate synthase or phosphoribosylanthranilate isomerase can be used as targets to facilitate design and/or identification of inhibitors of those enzymes that may be useful as herbicides. This is desirable because the anthranilate phosphoribosiltransferase, the indole-3-glycerol phosphate synthase and the phosphoribosylanthranilate isomerase described herein catalyze various steps in tryptophan biosynthesis. Accordingly, inhibition of the activity of one or more of the enzymes described herein could lead to inhibition plant growth. Thus, the instant anthranilate phosphoribosiltransferase, indole-3-glycerol phosphate synthase or phosphoribosylanthranilate isomerase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bematzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics*

16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the anthranilate phosphoribosiltransferase, the indole-3-glycerol phosphate synthase or the phosphoribosylanthranilate isomerase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an anthranilate phosphoribosiltransferase, an indole-3-glycerol phosphate synthase or a phosphoribosylanthranilate isomerase can be identified and obtained. This mutant plant can then be used to determine or confirm the natural function of the anthranilate phosphoribosiltransferase, the indole-3-glycerol phosphate synthase or the phosphoribosylanthranilate isomerase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn10 | Corn Developing Kernel (Embryo and Endosperm); 10 Days After Pollination | cbn10.pk0045.b8 |
| cco1 | Corn Cob of 67 Day Old Plants Grown in Green House | cco1.pk0002.f11 |
| cco1n | Corn Cob of 67 Day Old Plants Grown in Green House* | cco1n.pk0030.b11 |
| ceb1 | Corn Embryo 10 to 11 Days After Pollination | ceb1.pk0026.d2 |
| cen3n | Corn Endosperm 20 Days After Pollination* | cen3n.pk0147.h5 |
| chp2 | Corn 11 Day Old Leaf Treated 24 Hours With Herbicides** | chp2.pk0003.c4 |
| cr1n | Corn Root From 7 Day Old Seedlings* | cr1n.pk0121.b7 cr1n.pk0145.g6 |
| csi1 | Corn Silk | cs1.pk0056.d10 |
| p0002 | Corn Tassel: Premeiotic, Early Uninucleate | p0002.cgevb40r |
| p0022 | Mid Rib of the Middle ¾ of the 3rd Leaf Blade From Corn Green Leaves Treated with 1 mg/ml Jasmonic Acid in 0.02% Tween 20–24 Hours Before Collection* | p0022.cglne15r |
| p0037 | Corn V5 Stage Roots Infested With Corn Root Worm | p0037.crwan82r |
| p0041 | Corn Root Tips Smaller Than 5 mm in Length Four Days After Imbibition | p0041.crtav17rb |
| p0068 | Corn Pericarp 28 Days After Pollination | p0068.clsaa67r |
| p0091 | Corn Roots 2 and 3 Days After Germination, Pooled | p0091.cmarc86r |
| p0099 | Corn Tassel: Apical Meristem; Floral Transition | p0099.ctbai70r |
| p0103 | Corn Tassel Shoots (0.1–1.4 cm) | p0103.ciaag55r |
| p0104 | Corn Roots V5 Corn Root Worm Infested | p0104.cabbg36r |
| p0109 | Corn Leaves From Les9 Mutant***, Les9 Transition Zone and Les9 Mature Lesions, Pooled* | p0109.cdadc66r |
| p0128 | Corn Primary and Secondary Immature Ear | p0128.cpicq73r |
| rl0n | Rice 15 Day Old Leaf* | rl0n.pk0021.f11 |
| rsr9n | Rice Leaf 15 Days After Germination Harvested 2–72 Hours Following Infection With *Magnaporta grisea* (4360-R-62 and 4360-R-67)* | rsr9n.pk001.g2 |
| sdp2c | Soybean Developing Pods (6–7 mm) | sdp2c.pk001.f3 |
| ssm | Soybean Shoot Meristem | ssm.pk0059.f8 |
| wr1 | Wheat Root From 7 Day Old Seedling | wr1.pk0127.e10 |
| wre1 | Wheat Root From 7 Day Old Etiolated Seedling | wre1.pk0003.b12 |
| wre1n | Wheat Root From 7 Day Old Etiolated Seedling* | wre1n.pk0075.b10 |

*These libraries were normalized essentially as described in U.S. Pat. No. 5,482,845
**Application of 2-[(2,4-dihydro-2,6,9-trimethyl[1]benzothiopyrano[4,3-c]pyrazol-8-yl)carbonyl]-1,3-cyclohexanedione S,S-dioxide (synthesis and methods of using this compound are described in WO 97/19087, incorporated herein by reference) and 2-[(2,3-dihydro-5,8-dimethylspiro[4H-1-benzothiopyran-4,2'-[1,3]dioxolan]-6-yl)carbonyl]-1,3-cyclohexanedione S,S-dioxide (also named 2-[(2,3-dihydro-5,8-dimethylspiro[4H-1-benzothiopyran-4,2'-[1,3]dioxolan]-6-yl)carbonyl]-3-hydroxy-2-cyclohexen-1-one S,S-dioxide; synthesis and methods of using this compound are described in WO 97/01550, incorporated herein by reference)
***Les9 mutants are described by Hoisington, D. (1986) Maize Genet Coop News Lett 60:50–51.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding tryptophan biosynthetic enzymes were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Anthranilate Phosphoribosyltransferase

The BLASTX search using the EST sequences from several corn, soybean and wheat clones revealed similarity of the proteins encoded by the cDNAs to anthranilate phosphoribosyltransferase from *Arabidopsis thaliana*. In the process of comparing the corn ESTs it was found that clones cbn10.pk0045.b8, cco1.pk0002.f11 and cs1.pk0056.d10 had overlapping regions of homology. Using this homology it was possible to align the ESTs and assemble a contig (a contig is an assemblage of overlapping nucleic acid sequences to form one contiguous nucleotide sequence). The individual sequences were assembled into one contiguous nucleotide sequence encoding anthranilate phosphoribosyltransferase from corn. The database accession numbers and BLAST results for each of these ESTs and contigs are shown in Table 3:

TABLE 3

BLAST Results for Clones Encoding Polypeptides Homologous to Anthranilate phoshoribosyltransferase

| Clone | Database Organism | Accession No | Blast Score pLog |
|---|---|---|---|
| Contig of clones: cbn10.pk0045.b8 cco1.pk0002.f11 cs1.pk0056.d10 | *A. thaliana* | GenBank U58942 | 54.15 |
| wre1.pk0003.b12 | *A. thaliana* | GenBank U58942 | 47.39 |
| ssm.pk0059.f8 | *A. thaliana* | GenBank M96073 | 36.00 |

A longer corn contig was assembled with a portion of the cDNA inserts from clones p0037.crwan82r, p0022.cg1ne15r, cbn10.pk0045.b8, p0109.cdadc66r, cr1n.pk0145.g6, cco1.pk0002.f11, cs1.pk0056.d10, p0103.ciaag55r and p0104.cabbg36r and the sequence of the entire cDNA insert in clones ssm.pk0059.f8 and wre1.pk0003.b12 was determined. The BLASTX search using these sequences revealed similarity of the proteins encoded by the cDNAs to anthranilate phosphoribosyltransferase from *Arabidopsis thaliana* (NCBI General Identifier Nos. 1389768 and 401213). The BLAST results for each of these sequences are shown in Table 4:

TABLE 4

BLAST Results for Clones Encoding Polypeptides Homologous to Anthranilate Phosphoribosyltransferase

| | BLAST pLog Score | |
|---|---|---|
| Clone | 1389768 | 401213 |
| Contig of: p0037.crwan82r p0022.cg1ne15r cbn10.pk0045.b8 p0109.cdadc66r cr1n.pk0145.g6 cco1.pk0002.f11 cs1.pk0056.d10 p0103.ciaag55r p0104.cabbg36r | 159.0 | 159.0 |
| ssm.pk0059.f8 | 95.70 | 96.22 |
| wre1.pk0003.b12 | 96.10 | 96.00 |

The sequence of the contig assembled from a portion of the cDNA inserts from clones p0037.crwan82r, p0022.cg1ne15r, cbn10.pk0045.b8, p0109.cdadc66r, cr1n.pk0145.g6, cco1.pk0002.f11, cs1.pk0056.d10, p0103.ciaag55r and p0104.cabbg36r is shown in SEQ ID NO:1; the deduced amino acid sequence of this cDNA is shown in SEQ ID NO:2. The sequence of the entire cDNA insert from clone ssm.pk0059.f8 is shown in SEQ ID NO:3; the deduced amino acid sequence of this cDNA is shown in SEQ ID NO:4. The sequence of the entire cDNA insert from clone wre1.pk0003.b12 is shown in SEQ ID NO:5; the deduced amino acid sequence of this cDNA is shown in SEQ ID NO:6. BLAST scores and probabilities indicate that the instant nucleic acid fragments encode an almost entire conr anthranilate phosphoribosyltransferase and the C-terminal portions of soybean and wheat anthranilate phosphoribosyltransferase. These sequences represent the first corn, soybean and wheat sequences encoding anthranilate phosphoribosyltransferase.

Example 4

Characterization of Corn, Rice and Wheat cDNA Clones Encoding Indole-3-Glycerol Phosphate Synthase The BLASTX search using the EST sequences from several corn, rice and wheat clones revealed similarity of the proteins encoded by the cDNAs to indole-3-glycerol phosphate synthase from *Arabidopsis thaliana*. In the process of comparing the corn ESTs it was found that clones cr1n.pk0121.b7 and cen3n.pk0047.d8 had overlapping regions of homology. A comparison of the wheat ESTs from clones wre1n.pk0075.b10 and wle1n.pk0039.d2 also had overlapping regions of homology. Using this homology it was possible to align the ESTs and assemble contigs (a contig is an assemblage of overlapping nucleic acid sequences to form one contiguous nucleotide sequence). The individual sequences were assembled into unique contiguous nucleotide sequences encoding indole-3-glycerol phosphate synthase from corn and wheat. The database accession numbers and BLAST results for each of these ESTs and contigs are shown in Table 5:

TABLE 5

BLAST Results for Clones Encoding Polypeptides Homologous to Indole-3-Glycerol Phosphate Synthase

| Clone | Database Organism | Accession No | Blast Score pLog |
|---|---|---|---|
| Contig of clones: cr1n.pk0121.b7 cen3n.pk0047.d8 | *A. thaliana* | U18770 | 50.69 |
| cen3n.pk0147.h5 | *A. thaliana* | U18770 | 19.15 |
| r10n.pk0021.f11 | *A. thaliana* | U18770 | |
| Contig of clones: wre1n.pk0075.b10 wle1n.pk0039.d2 | *A. thaliana* | U18770 | 56.39 |
| wl1n.pk0112.b3 | *A.thaliana* | U18770 | 31.00 |

The sequence of the entire cDNA insert in clone cen3n.pk0147.h5 was determined and is shown in SEQ ID NO:7; the deduced amino acid sequence of this cDNA is shown in SEQ ID NO:8. A contig was assembled using the sequence of the entire cDNA insert in clones cr1n.pk0121.b7 and chp2.pk0003.c4 and the EST sequences in clones p0128.cpicq73r, p0041.crtav17rb, p0002.cgevb40r and p0091.cmarc86r. The sequence of this contig is shown in SEQ ID NO:9; the deduced amino acid sequence of this cDNA is shown in SEQ ID NO:10. The amino acid sequence set forth in SEQ ID NO:8 was evaluated by BLASTP, yielding a pLog value of 108.0 versus the *Arabidopsis thaliana* sequence. The sequence of the entire cDNA insert in clone r10n.pk0021.f11 was determined and is shown in SEQ ID NO:11; the deduced amino acid sequence of this cDNA is shown in SEQ ID NO:12. The sequence of the entire cDNA insert in clone wre1n.pk0075.b10 was determined and is shown in SEQ ID NO:15; the deduced amino acid sequence of this cDNA is shown in SEQ ID NO:16.

Sequence alignments and BLAST scores and probabilities indicate that the instant nucleic acid fragments encode an entire corn indole-3-glycerol phosphate synthase and portions of corn, rice and wheat indole-3-glycerol phosphate synthase. These sequences represent the first corn, rice and wheat sequences encoding indole-3-glycerol phosphate synthase.

Example 5

Characterization and Expression in Microbial Cells of a Soybean cDNA Clone Encoding Indole-3-Glycerol Phosphate Synthase The BLASTX search using the EST sequences from clone sdp2c.pk001.f3 revealed similarity of the proteins encoded by the cDNAs to indole-3-glycerol phosphate synthase precursor from *Arabidopsis thaliana* (NCBI General Identifier No. 1351303) with a pLog value of 12.15. The sequence of the entire cDNA insert in clone sdp2c.pk001.f3 was determined and is shown in SEQ ID NO:13; the deduced amino acid sequence of this cDNA is shown in SEQ ID NO:14. Bacteria containing clone sdp2c.pk001.f3 were obtained from the DuPont Genomics group and the plasmid isolated. The PCR cloning strategy outlined by Zeng G. (1998) *Biotechniques* 25:206–208 was used to clone the isolated fragment into plasmid pBX2 for expression of the protein in bacterial cells. The PCR primers used were:

```
                                         SEQ ID NO:27
pIGSs-F1: 5'- TATG GAA GGT TTG GCT TCC CTC -3'

SEQ ID NO:28
pIGSs-F2: 5'- TG GAA GGT TTG GCT TCC CTC -3'

SEQ ID NO:29
pIGSs-M1: 5'- TATG GTT CTG AAA ATT AAG GAG TGG -3'

SEQ ID NO:30
pIGSs-M2: 5'- TG GTT CTG AAA ATT AAG GAG TGG -3'

SEQ ID NO:31
pSK-B1:   5'- GATCC ATA GGG GCA ATT GGG TAC CGG -3'

SEQ ID NO:32
pSK-B2:   5'- C ATA GGG GCA ATT GGG TAC CGG -3'
```

Primers with an F designation were used to isolate clones with a chloroplast transit peptide sequence (CTP) while those designated with an M were used to isolate clones for the mature protein (no CTP). Primers with pSKB designation are generic primers for use with the pBluescript SK plasmid. PCR reactions were performed with the Expand High Fidelity PCR System of Boehringer Mannheim. Four different PCR reactions were performed with the following primer combinations:

Reaction 1: pIGSs-F2 with pSKB1; the DNA obtained will be referred to as F2B1;

Reaction 2: pIGSs-F1 with pSKB2; the DNA obtained will be referred to as F1B2;

Reaction 3: pIGS-M2 with pSKB1; the DNA obtained will be referred to as M2B1;

Reaction 4: pIGS-M1 with pSKB2; the DNA obtained will be referred to as M1B2.

PCR was performed with a touchdown program: 94° C. for 3 minutes; 94° C. for 15 sec, 66° C. for 30 sec (to 57° C. in 10 cycles), 72° C. for 1 min 30 sec; 94° C. for 15 sec, 57° C. for 30 sec, 72° C. for 1 min 30 sec (25 cycles); 72° C. 7 min; hold at 4° C. until use. PCR products were separated using a 1% agarose TAE gel and DNA in bands was purified using the Qiaex II agarose gel extraction protocol from Qiagen. The final DNA product was eluted in 40 μL of 10 mM Tris-HCl, Ph 8.5. M1B2 was pooled with M2B1 and concentrated to 25 μL total volume using a speed vac. F1B2 was pooled with F2B1 and concentrated to 25 μL total volume using a speed vac. The concentrated mixtures were heated to 95° C. and allowed to cool down to room temperature over about 20 minutes. Ligations were set up with 1 µL of Nde I/Bam HI-digested pBX2, 5 µL water, 2 µL T4 DNA ligase 5×buffer (Gibco/BRL), 1 µL T4 DNA ligase(Gibco/BRL) and either 1 µL of M1B2+M2B1 (for ligation 1) or 1 µL F1B2+F2B1 (for ligation 2). Ligations proceeded at room temperature for 4 hours. The ligation mix was transformed into DH5alpha competent *E. coli* using standard heat shock methods, plated onto LB/carbenicillin plates and grown overnight at 37° C. Plasmids with the correct inserts were identified by double digest of miniprep DNA using Nde I and Bam HI. Plasmid containing the full-length gene is pBX2-IGPS-3 and plasmid containing the gene for the mature protein (no putative chloroplast transit peptide sequence) is pBX2-IGPS-4. Two separate colonies for each construct were used for midi plasmid preps. The identity of the resulting DNA was confirmed by DNA sequencing.

The plasmid DNAs were also transformed into BL21 (DE3) pLysS cells using a rapid transformation protocol (Pope B. and Kent H. M. (1996) *Nucleic Acids Research* 24:536–537) and bacteria grown on LB/carbenicillin/chloramphenicol plates overnight at 37° C. Colonies were selected and streaked for isolation. Well-isolated colonies were used to produce frozen glycerol stocks.

For protein production, LB/carbenicillin/chloramphenicol plates were streaked with the appropriate glycerol stock and grown overnight at 37° C. A single well-isolated colony was used to inoculate 1 liter of liquid LB (100 µg/mL carbenicillin, 34 µg/mL chloroamphenicol). Bacteria was grown at room temperature (26° C.) until reaching an optical density of between 0.4 and 1.0 at 600 nm. IPTG was added to a final concentration of 0.5 mM and bacteria subsequently harvested by centrifugation 4 hours later. Bacterial pellets were stored at −80° C. until use. Pellets were thawed in extraction buffer which consisted of 300 mM NaCl, 10 mM imidazole, 10% glycerol, 10 mM β-mercaptoethanol, 0.1% Triton X-100, 20 mM HEPES, 1 mM AEBSF (protease inhibitor), 1 µg/mL leupeptin (protease inhibitor), 1 µg/ml antipain (protease inhibitor), pH 7.9. All subsequent steps were performed on ice or in a cold room. DNA in the extracts was sheared using a probe sonicator and then extracts clarified through centrifugation. 0.5 mL of Qiagen Ni-NTA agarose was added to each supernatant and then extracts placed on an end-over-end mixer for 1 hour. Ni-NTA agarose was transferred to a column and resin washed several times with extraction buffer. IGPS protein was eluted with 1 mL of elution buffer (extraction buffer minus protease inhibitors and containing 250 mM imidazole instead of 10 mM imidazole).

Enzyme assays were performed on a SLM Aminco 8000 spectrofluorometer with all slits set to 16 nm, excitation 280 nm, emission 350 nm, gain 100, HV 250. The assay was based on Hankins, C. N. et al. (1975) *Anal Biochem* 69:510–517. Assay buffer was pH 7.9 and contained 50 mM EPPS, 1 mM DTT, 10% glycerol, 5 mM EDTA, and 100 µg/L BSA. Using 8 µM of 1-(2-carboxyphenylamino)-1-deoxyribulose-5-phosphate (CdRP) substrate prepared according to Kirschner K et al. (1987) *Methods Enzymol* 142:386–397 the following activities were measured:

TABLE 6

Activity of Cloned *Arabidopsis* and Soybean Indole-3-Glycerol Phosphate Synthase

| Protein | Fluorescent units/µg protein* |
|---|---|
| IGPS1 (*Arabidopsis*)** | 1.48 ± 0.12 |
| IGPS3*** | 3.09 ± 0.22 |
| IGPS4**** | 4.36 ± 0.25 |

*mean ± spread of two determinations
**Arabidopsis indole-3-glycerol phosphate synthase gene (GenBank Accession No. U18770) was placed in the pBX2 vector essentially by the method described above. Enzymatically active recombinant protein expression has not been previously reported for this gene.
***Protein purified from cells harboring the pBX2-IGPS-3 plasmid.
****Protein purified from cells harboring the pBX2-IGPS-4 plasmid.

The pH optimum for all three proteins was 7.9. Km for IGPS 1 is 3 µM and IGPS4 is 2 µM. Fluorescent units are not converted to amount of product since a sample of indole-3-glycerolphosphate is not available to create a standard curve. The data indicate that the instant nucleic acid fragments encode an enzyme with Indole-3-Glycerol Phosphate Synthase activity. Availability of the instant nucleic acid fragments and assays for enzyme activity will facilitate screening of chemical compounds for inhibitor activity and will lead to the discovery and development of herbicidal compounds.

FIGS. 2A and 2B presents an alignment of the amino acid sequences set forth in SEQ ID NOs: 10 and 14 and the *Arabidopsis thaliana* indole-3-glycerol phosphate synthase sequence (SEQ ID NO:27). The amino acid sequence set forth in SEQ ID NO: 10 54.3% similar to the *Arabidopsis thaliana* sequence while the amino acid sequence set forth in SEQ ID NO:14 is 67.9% similar to the *Arabidopsis thaliana* sequence. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABJOS*. 5:151–153) with the default parameters (GAP PENALTY=10, GAP LENGTH PENALTY=10).

Sequence alignments and BLAST scores and probabilities indicate that the instant nucleic acid fragment encodes an entire enzymatically active soybean indole-3-glycerol phosphate synthase. This sequence represents the first soybean sequence encoding indole-3-glycerol phosphate synthase.

Example 6

Characterization of cDNA Clones Encoding Phosphoribosylanthranilate Isomerase

The BLASTX search using the EST sequences from several corn and wheat clones revealed similarity of the proteins encoded by the cDNAs to phosphoribosylanthranilate isomerase from *Arabidopsis thaliana*. In the process of comparing the corn ESTs it was found that clones ceb1.pk0026.d2 and csi1n.pk0048.f11 had overlapping regions of homology. A comparison of the wheat ESTs from clones wr1.pk0127.e10 and wr1.pk0102.b8 also had overlapping regions of homology. Using this homology it was possible to align the ESTs and assemble contigs (a contig is an assemblage of overlapping nucleic acid sequences to form one contiguous nucleotide sequence). The individual sequences were assembled into unique contiguous nucleotide sequences encoding anthranilate phosphoribosyltransferase from corn and wheat. The database accession numbers and BLAST results for each of these ESTs and contigs are shown in Table 7:

TABLE 7

BLAST Results for Clones Encoding Polypeptides Homologous to Phosphoribosylanthranilate Isomerase

| Clone | Database Organism | Accession No | Blast Score pLog |
|---|---|---|---|
| Contig of clones: ceb1.pk0026.d2 csi1n.pk0048.f11 | A. thaliana | GenBank U18969 | 14.39 |
| Contig of clones: wr1.pk0127.e10 wr1.pk0102.b8 | A. thaliana | GenBank U34757 | 7.22 |

The BLASTX search using the sequences of the contig assembled from clones cco1n.pk0030.b11, p0068.c1saa67r and p0099.ctbai70r, using the EST sequences from clone rsr9n.pk001.g2 and using the sequence of the entire cDNA insert in clones ceb1.pk0026.d2 and wr1.pk0127.e10 revealed similarity of the proteins encoded by the cDNAs to Phosphoribosylanthranilate Isomerase from *Arabidopsis thaliana* (NCBI General Identifier No. 619749). The BLAST results for each of these sequences are shown in Table 8:

TABLE 8

BLAST Results for Clones Encoding Polypeptides Homologous to Phosphoribosylanthranilate Synthase

| Clone | BLAST pLog Score 619749 |
|---|---|
| cco1n.pk0030.b11 p0068.c1saa67r p0099.ctbai70r | 37.00 |
| ceb1.pk0026.d2 | 82.70 |
| rsr9n.pk001.g2 | 45.70 |
| wr1.pk0127.e10 | 80.52 |

The sequence of the contig assembled from a portion of the cDNA insert from clones cco1n.pk0030.b11, p0068.c1saa67r and p0099.ctbai70r is shown in SEQ ID NO:17; the deduced amino acid sequence of this cDNA is shown in SEQ ID NO:18. The sequence of the entire cDNA insert in clone ceb1.pk0026.d2 was determined and is shown in SEQ ID NO:19; the deduced amino acid sequence of this cDNA is shown in SEQ ID NO:20. The nucleotide sequence set forth in SEQ ID NO:19 includes the sequence from a portion of the cDNA insert in clone csi1n.pk0048.f11. The amino acid sequence set forth in SEQ ID NO:20 was evaluated by BLASTP, yielding a pLog value of 74.0 versus the *Arabidopsis thaliana* sequence. The sequence of a portion of the cDNA insert from clone rsr9n.pk001.g2 is shown in SEQ ID NO:21; the deduced amino acid sequence of this cDNA is shown in SEQ ID NO:22. The sequence of the entire cDNA insert in clone wr1.pk0127.e10 was determined and is shown in SEQ ID NO:23; the deduced amino acid sequence of this cDNA is shown in SEQ ID NO:24. The nucleotide sequence set forth in SEQ ID NO:23 includes the sequence from a portion of the cDNA insert in clonewr1.pk0102.b8. The amino acid sequence set forth in SEQ ID NO:24 was evaluated by BLASTP, yielding a pLog value of 72.00 versus the *Arabidopsis thaliana* sequence.

FIGS. 3A and B presents an alignment of the amino acid sequences set forth in SEQ ID NOs:20 and 24 and the *Arabidopsis thaliana* phosphoribosylanthranilate isomerase sequence. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) CABIOS. 5:151–153) with the default parameters (GAP PENALTY=10, GAP LENGTH PENALTY=10).

Sequence alignments and BLAST scores and probabilities indicate that the instant nucleic acid fragments encode entire or nearly entire corn and wheat phosphribosylanthranilate isomerase and portions of corn and rice phosphoribosylanthranilate isomerase. These sequences represent the first corn, rice and wheat sequences encoding phosphoribosylanthranilate isomerase.

Example 7

Expression of Chimeric Genes in Monocot Cells

A chimeric gene comprising a cDNA encoding a tryptophan biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U. S. Biochemical). The resulting plasmid construct would comprise a chimeric gene encoding, in the 5' to 3' direction, the maize 27 kD zein promoter, a cDNA fragment encoding a tryptophan biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (From et al., (1990) *Bio/Technology* 8:833–839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant tryptophan biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding a tryptophan biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the tryptophan biosynthetic enzyme and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant tryptophan biosynthetic enzyme can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the tryptophan biosynthetic enzyme are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 10

Evaluating Compounds for Their Ability to Inhibit the Activity of Tryptophan Biosynthetic Enzymes The tryptophan biosynthetic enzymes described herein may be produced using any number of methods known to those skilled in the art. Such methods include, but are not limited to, expression in bacteria as described in Example 9, or expression in eukaryotic cell culture, in planta, and using viral expression systems in suitably infected organisms or cell lines. The instant tryptophan biosynthetic enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant tryptophan biosynthetic enzymes, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the tryptophan biosynthetic enzymes are expressed as fusion proteins, the purification protocol may include the use of an affinity resin which is specific for the fusion protein tag attached to the expressed enzyme or an affinity resin containing ligands which are specific for the enzyme. For example, a tryptophan biosynthetic enzyme may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the tryptophan biosynthetic enzymes disclosed herein. Assays may be conducted under well known experimental conditions which permit optimal enzymatic activity. For example, assays for anthranilate phosphoribosyltransferase are presented by Hommel, U. et al. (1989) *Eur J Biochem* 180:33–40. Assays for indole-3-glycerol phosphate synthase are presented by Hankins, C. N. et al. (1975) *Anal Biochem* 69:510–517). Assays for phosphoribosylanthranilate isomerase are presented by Last, R. L. and Fink, G. R. (1988) *Science* 240:305–310.

APPENDIX A

Clustal V alignment of the corn and wheat phosphoribosyl-anthranilate isomerase amino acid sequences of the present invention (SEQ ID NO:20 and SEQ ID NO:24, respectively) with the phosphoribosylanthranilate isomerase amino acid sequences of *Arabidopsis thaliana*, *Saccharomyces cerevisiae*, and *E. coli* found in the Li et al. alignment (AtPAI1, ATPAI2, AtPAI3, yeast, and *E. coli*, respectively). The conserved domains found in the Li et al. article are shown boxed, and the invariant and conserved residues from Sterner et al. are indicated above the alignment. The invariant residues are in upper case letters and the conserved residues are in lower case. The program uses dashes to maximize the alignment.

```
                             K CG                       ga         G
  1 MLLASSTRRYEQFPLA--RNNGLPRFSRVKMSC--LGTNQSNHHSDTVRSS---SPSCGD    SEQ ID 20
  1 MATAFSTKQPLRVATP--TNKWRPRLPLIKMQY-----SSNKRASASISLP---SSAEGV    SEQ ID 24
  1 MSTGISTDLHVHFGALNFSKTYKSGLSNRTVSFSRVGYAQNRKLSCSVSNTENVAPKDDE    AtPAI1
  1 MSTGISTDLHVHFGALNFSKTYKSGLSNRTVSFSRVGYAQNRKLSCSVSNTENVAPKDDE    AtPAI2
  1 MSTGISSDLHLHPRALNFSKTSKSGLSNRKVSFSSVGYAQNRKLSCSVSSTENVAPKDDD    AtPAI3
  1 N-----------------------------------------------------------    E coli
  1 MSV-----------INFT-----------------------------------------    yeast
        ----------+---------+---------+---------+---------+---------+
              10        20        30        40        50        60
                              V VFV                QlHg
 54 TRKVHPVVKMCGITSARDAEMAVKAGAELIGMILWPNSKRSVSLLEAKEISRVVQSYGAE    SEQ ID 20
 51 ERN-EPIVKMCGITSARDAEFAAKAGAKLIGMILWPKSKRSVQRSEAKEISRVAKSYGAE    SEQ ID 24
 61 RGKDRPLVKMCGITSARDAAMAVEAGADFIGMIIWPHSKRSISLSVAKDISKVAREGGAK    AtPAI1
 61 RGKDRPLVKMCGITSARDAAMAVEAGADFIGMIIWPHSKRSISLSVAKDISKVAREGGAK    AtPAI2
 61 RGKDRPLVKMCGITSARDAAMAVEAGADFIGMIIWPHSKRSISLSVAKDISQVAREGGAK    AtPAI3
  2 --------KVCGLTRGQDAKAAYDAGAIYGGLIFVATSPRCVNVEQAQEV---------M    E coli
  8 -GSSGPLVKVCGLQSTEAAECALDSDADLLGIICVPNRKRTIDPVIARKISSLVKAYKNS    yeast
        ----------+---------+---------+---------+---------+---------+
              70        80        90       100       110       120
                                                              laGGl
                                        D         G G
114 S------ VGVFV DDNEETILRVSDSCDLNF VQLHG DESRALVHTLSKNNRIVYVLNADDD   SEQ ID 20
110 A------ VGVFV DDDEETILRVADSCNLQL IQLHG DSSRALVPALAKNNRIVYVLNADAD   SEQ ID 24
121 P------ VGVFV EDDENTILRAADSSDLEL VQLHG NGSRAAFSRLVRKRRVIYVLNANQD   AtPAI1
121 P------ VGVFV EDDDNTILRAADSSDLEL VQLHG NGSRAAFSRLVRKRRVIYVLNANQD   AtPAI2
121 P------ VGVFV EDDENTILRAADSSDLEL VQLHG NSSRAAFSRLVRERKVIYVLNANED   AtPAI3
 45 AAAPLQY VGVFR NHDIADVVDKAKVLSLVA VQLHG NEEQLYIDTL--REALPAHVAIWKA   E coli
 67 SGTPKYL VGVFR NQPKEDVLALVNDYGIDI VQLHG DESWQEYQEFLGLPVIKRLVFPKDC   yeast
       ------- --+-- -------+---------+ ----- ----+---------+---------+
             130       140       150        160       170       180
                    D       G G                              laGGl
168 GKLINIPDIE-YEL-DWYLVDSAK GGSGKGFNWQKFQMPSVKSKNG-----WL LAGGL HA    SEQ ID 20
164 GKLINSPPSEEYDI-DWFLVDSAE GGSGKGFNWDNFRMPSVKSKNG-----WL LAGGL HA    SEQ ID 24
175 GKLLNEVPEEDCHLADWILVDSAT GGSGHGFNWAQFKLPSVRSRNG-----WL LAGGI NP    AtPAI1
175 GKLLNEVPEEDCHLADWILVDSAT GGSGHGFNWAQFKLPSVRSRNG-----WL LAGGI NP    AtPAI2
175 GKLLNVVPEEDGHLADWILVDSAT GGSGKGFNWAQFKLPSVRSRNG-----WL LAGGI NP    AtPAI3
103 LSVGETLPAREFQHVDKYVLDNGQ GGSGQRFDWSLL--------NGQTLGNVL LAGGL GA    E coli
127 NILLSAASQKPHSFIP--LFDSEA GGTGELLDWNSISDWVGRQESPESL-HFM LAGGL TP    yeast
       ---------+---------+---- -----+---------+---------+--- ----- -+
             190       200      210       220       230      240
            N          D   sgv       G    d
221 DNVCEAFSALKPD GVDVSSGI CGRDGIRKDADRINSFISNVKSLN-----FLS          SEQ ID 20
218 DNVCQAASALKPN GVDVSSGI CSPDGISKDPKRISSFMRSVQSLSSRRGLYLDAPGLL     SEQ ID 24
230 TNVSEALSILQPD GIDVSSGI CGTDGIQKDKSKISSFITAVRSVH-----Y            AtPAI1
230 TNVSEALSILQPD GIDVSSGI CGTDGIQKDKSKISSFITAVRSVH-----Y            AtPAI2
230 TNVSEALSILQPD GIDVSSGI CGIDGIQKDKSKISSFITAVRSVH-----Y            AtPAI3
155 DNCVEA-AQTGCA GLDFNSAV ESQPGI-KDARLLASVFQTLRA-------Y            E coli
184 ENVGDALRLNGVI GVDVSGGV -ETNGV-KDSNKIANFVKNAKK                     yeast
       ---------+--- ------+- --------+---------+---------+--------
             250       260       270       280       290
```

What is claimed is:

1. An isolated polynucleotide comprising:
   (a) a nucleotide sequence encoding a polypeptide having phosphoribosylanthranilate isomerase activity, wherein the amino acid sequence of the polypeptide and the amino acid sequence of SEQ ID NO:20 have at least 90% identity, or
   (b) the complement of the nucleotide sequence.
2. The polynucleotide of claim 1, wherein the amino acid sequence of the polypeptide and the amino acid sequence of SEQ ID NO:20 have at least 95% identity.
3. The polynucleotide of claim 1, wherein the nucleotide sequence comprises the nucleotide sequence of SEQ ID NO:19.
4. The polynucleotide of claim 1, wherein the amino acid sequence of the polypeptide comprises the amino acid sequence of SEQ ID NO:20.
5. A vector comprising the polynucleotide of claim 1.
6. A chimeric gene comprising the polynucleotide of claim 1 operably linked to a regulatory sequence.
7. A method for transforming a cell comprising transforming a cell with the polynucleotide of claim 1.
8. An isolated cell comprising the chimeric gene of claim 6.
9. A method for producing a plant comprising transforming a plant cell with the polynucleotide of claim 1 and regenerating a plant from the transformed plant cell.
10. A plant comprising the chimeric gene of claim 6.
11. A seed comprising the chimeric gene of claim 6.
12. A method for producing a polypeptide encoded by the chimeric gene of claim 6 comprising:
   (a) transforming a cell with the chimeric gene; and
   (b) culturing said cell in a medium to promote expression of the polypeptide encoded by the chimeric gene.

* * * * *

UNITED STATES PATENT AND TRADEMARK OFFICE
CERTIFICATE OF CORRECTION

PATENT NO. : 7,192,758 B2
APPLICATION NO. : 10/295220
DATED : March 20, 2007
INVENTOR(S) : Rebecca E. Cahoon, Steven Gutteridge and Steven Vollmer It is certified that error appears in the above-identified patent and that said Letters Patent is hereby corrected as shown below:

Col. 68, line 25, Claim 8, insert --, wherein said cell is a microbial or a plant cell-- after "claim 6".

Signed and Sealed this

Thirteenth Day of November, 2007

JON W. DUDAS
*Director of the United States Patent and Trademark Office*

SEQUENCE LISTING

<160> NUMBER OF SEQ ID NOS: 32

<210> SEQ ID NO 1
<211> LENGTH: 1659
<212> TYPE: DNA
<213> ORGANISM: Zea mays
<220> FEATURE:
<221> NAME/KEY: unsure
<222> LOCATION: (1248)
<223> OTHER INFORMATION: n = a, c, t, or g
<220> FEATURE:
<221> NAME/KEY: unsure
<222> LOCATION: (1553)
<223> OTHER INFORMATION: n = a, c, t, or g
<220> FEATURE:
<221> NAME/KEY: unsure
<222> LOCATION: (1636)
<223> OTHER INFORMATION: n = a, c, t, or g
<220> FEATURE:
<221> NAME/KEY: unsure
<222> LOCATION: (1640)
<223> OTHER INFORMATION: n = a, c, t, or g

<400> SEQUENCE: 1

```
cgcgtcgctc aagttcgcct cccccaaacc cttggcctcc gcaccgtccg cgctcctttg      60
cgggcgtcgc gcccaggcgc ggcccctccc agcaagtcgc ctccctccgc ctacccgcgt     120
cgccgtgcag ccccccgccg cgccggtcgc gacgcgcatc ggctcctttg acaaggtgct     180
ggaggcgctg atcggcggga ccgacttctc gaggaggat gcggaggcga cgctgaagct      240
gctcctggac gagaaggacg aggcgcgcat ctccgccttc ctcgtcctcc tcagggccaa     300
gggcgagacc ttcgaagaga tcgtgggggct tgcgaaggcg atgttgagct gctgcatccg    360
agtcgatggt ctggacgacg ccgtcgacat tgtcgggaca ggcggcgacg gcgcagacac     420
cgtcaacatc tccaccgggt ccaccatcct cgccgccgcg gccggcgcca aggtcgctaa     480
gcaaggaagc agggctagct cgtcggcgtg cggcagcgcc gatgtgctgg aggcgcttgg     540
ggtcaacatc gagcttggac ccgagggtat taaacaatgt gtcaatgagg tgggtgttgg     600
attcatgatg tctgcaaatt atcatcctgc aatgaaaatt gtcagacctg tgaggaagaa     660
gcttaaaata aagacagttt tcaatatcct tggtcctcta ctgaatccag caagggtgcc     720
tcatgctgtt attggtgttt accatgagaa tatagttacc aagatggcta aggctgctca     780
gaaatttgga atgaagagag cattggtcgt ccattcaaag ggtttggatg aaataagccc     840
acttggtccc ggatatatcc ttgatgttac tccagagaag attgaaaaaa tgttcttcga     900
tccattggat tttggcattc ctcgctgcac attggaagat ctgaaaggag gcgatccagc     960
gtttaatgca aaagttctcc aggatgttct tgctggtcaa aggggggcga ttgcagatgc    1020
ccttgttcta aatgctgcgg cgtccctact tgtcagtggt aaagtgaaaa atttacatga    1080
cggtgttgct ttagcacagg agacacagcg gtccgggaaa gccatcaata cacttgagtc    1140
ttggataaaa aaatcaaata gttccagaga ctgagtgaag ttgagtagca atagatggat    1200
ttctgcaata agacatgagg aatggtagca ataagggct ccgctgantc catccatcat     1260
ccgtgtatga ttggctttct tctcgtgttt tgttcatgat ttgtgtcaga aacctaggtg    1320
gcatctagtc tggtttatgt attgccagtg ctgttgtgta caaaaatctc cgtcgatatt    1380
ctaagctttt tggttagaaa ggtgcgctct tcattgtcct tgacggaact cggggtagat    1440
gaacataggc catctgttgt gatcttgtga tgctgcatta cgtttgcaat ggatcatata    1500
ttatgcaatg gcatgggaaa gattataccc atttgtaatg ggggaagaat canggcttaa    1560
```

```
acatttctac aataacgtgc gaacatttgt ccccattggt tacgcatgtc ctgaaatatg    1620
aataaagctg cagcantttn atattttgca aaaaaaaaa                           1659
```

<210> SEQ ID NO 2
<211> LENGTH: 390
<212> TYPE: PRT
<213> ORGANISM: Zea mays

<400> SEQUENCE: 2

```
Ala Ser Leu Lys Phe Ala Ser Pro Lys Pro Leu Ala Ser Ala Pro Ser
 1               5                  10                  15

Ala Leu Leu Cys Gly Arg Arg Ala Gln Ala Arg Pro Leu Pro Ala Ser
            20                  25                  30

Arg Leu Pro Pro Thr Arg Val Ala Val Gln Pro Ala Ala Pro
        35                  40                  45

Val Ala Thr Arg Ile Gly Ser Phe Asp Lys Val Leu Glu Ala Leu Ile
    50                  55                  60

Gly Gly Thr Asp Phe Ser Glu Glu Asp Ala Glu Ala Thr Leu Lys Leu
65                  70                  75                  80

Leu Leu Asp Glu Lys Asp Glu Ala Arg Ile Ser Ala Phe Leu Val Leu
                85                  90                  95

Leu Arg Ala Lys Gly Glu Thr Phe Glu Glu Ile Val Gly Leu Ala Lys
            100                 105                 110

Ala Met Leu Ser Cys Cys Ile Arg Val Asp Gly Leu Asp Asp Ala Val
        115                 120                 125

Asp Ile Val Gly Thr Gly Gly Asp Gly Ala Asp Thr Val Asn Ile Ser
    130                 135                 140

Thr Gly Ser Thr Ile Leu Ala Ala Ala Gly Ala Lys Val Ala Lys
145                 150                 155                 160

Gln Gly Ser Arg Ala Ser Ser Ser Ala Cys Gly Ser Ala Asp Val Leu
                165                 170                 175

Glu Ala Leu Gly Val Asn Ile Glu Leu Gly Pro Glu Gly Ile Lys Gln
            180                 185                 190

Cys Val Asn Glu Val Gly Val Gly Phe Met Met Ser Ala Asn Tyr His
        195                 200                 205

Pro Ala Met Lys Ile Val Arg Pro Val Arg Lys Leu Lys Ile Lys
    210                 215                 220

Thr Val Phe Asn Ile Leu Gly Pro Leu Leu Asn Pro Ala Arg Val Pro
225                 230                 235                 240

His Ala Val Ile Gly Val Tyr His Glu Asn Ile Val Thr Lys Met Ala
                245                 250                 255

Lys Ala Ala Gln Lys Phe Gly Met Lys Arg Ala Leu Val Val His Ser
            260                 265                 270

Lys Gly Leu Asp Glu Ile Ser Pro Leu Gly Pro Gly Tyr Ile Leu Asp
        275                 280                 285

Val Thr Pro Glu Lys Ile Glu Lys Met Phe Phe Asp Pro Leu Asp Phe
    290                 295                 300

Gly Ile Pro Arg Cys Thr Leu Glu Asp Leu Lys Gly Gly Asp Pro Ala
305                 310                 315                 320

Phe Asn Ala Lys Val Leu Gln Asp Val Leu Ala Gly Gln Arg Gly Ala
                325                 330                 335

Ile Ala Asp Ala Leu Val Leu Asn Ala Ala Ala Ser Leu Leu Val Ser
            340                 345                 350
```

-continued

```
Gly Lys Val Lys Asn Leu His Asp Gly Val Ala Leu Ala Gln Glu Thr
        355                 360                 365

Gln Arg Ser Gly Lys Ala Ile Asn Thr Leu Glu Ser Trp Ile Lys Lys
    370                 375                 380

Ser Asn Ser Ser Arg Asp
385                 390

<210> SEQ ID NO 3
<211> LENGTH: 981
<212> TYPE: DNA
<213> ORGANISM: Glycine max
<220> FEATURE:
<221> NAME/KEY: unsure
<222> LOCATION: (403)
<223> OTHER INFORMATION: n = a, c, t, or g

<400> SEQUENCE: 3
gcacgaggat gtgttggaag ctttgggagt ggtcattgac ttaggtccac agggggtgaa      60
gaggtgtgtg gatgaagctg ggatggggtt tatgatgtct acaaagtatc acccatcaat     120
gaagattgtc aggcctgtaa gaaagaagct aaagataaaa actatattca atatattggg     180
tccaatgttg aatccagcac atgccccttt tgccgttgtt ggagtataca cagaggactt     240
ggtccttaaa atggccaaag cactcaatag atttggcatg aaacgagcct tagttgtcca     300
ctctgaaggt ttgatgaaa tgagtcctct tggacctggt atagtgcttg atgttatggc     360
tgacagggtt gataagtttg catttgatcc ctattgttta ttnggaacag tggagtttgg     420
cattccacgg tgcaatattg aaagcttaaa aggtggtggt ccagaataca atgcagaggt     480
tttgaagcgt gttctaggtg gagagagagg gccaattgca gatgctttga ttctcaatgc     540
cgcagcagct ctcttagtca gtggctgtgt aagtaaccta gctgaagggg tttctgtggc     600
acgtgaaaca caacaatcag gaaaggctct gaaaacactc aacctgttga aggatgtctc     660
aaataacatc aaagatgagt tgggcatgga tgcctgaatt gttttgtggc ccaggttgtg     720
agttttgtaa acttgattca aacaagagga gcttggaagg cctcatatag tacatgtatt     780
attaaagaga tgtacaaaaa taatttaatt tattattgta aaattattta cccttcagta     840
ctgtgcaaaa aggttttaga attagttaag aaggattata atttgttttc atttatcatg     900
tcacttgaca aagtgacata ggaaatggat ttttttatct gaaaaagat tgagattcga     960 tgtaaaaaaa aaaaaaaaaa a                                              981

<210> SEQ ID NO 4
<211> LENGTH: 231
<212> TYPE: PRT
<213> ORGANISM: Glycine max
<220> FEATURE:
<221> NAME/KEY: UNSURE
<222> LOCATION: (134)
<223> OTHER INFORMATION: XAA = ANY AMINO ACID

<400> SEQUENCE: 4

His Glu Asp Val Leu Glu Ala Leu Gly Val Val Ile Asp Leu Gly Pro
  1               5                  10                  15

Gln Gly Val Lys Arg Cys Val Asp Glu Ala Gly Met Gly Phe Met Met
             20                  25                  30

Ser Thr Lys Tyr His Pro Ser Met Lys Ile Val Arg Pro Val Arg Lys
         35                  40                  45

Lys Leu Lys Ile Lys Thr Ile Phe Asn Ile Leu Gly Pro Met Leu Asn
     50                  55                  60
```

```
Pro Ala His Ala Pro Phe Ala Val Val Gly Val Tyr Thr Glu Asp Leu
 65                  70                  75                  80
Val Leu Lys Met Ala Lys Ala Leu Asn Arg Phe Gly Met Lys Arg Ala
                 85                  90                  95
Leu Val Val His Ser Glu Gly Leu Asp Glu Met Ser Pro Leu Gly Pro
            100                 105                 110
Gly Ile Val Leu Asp Val Met Ala Asp Arg Val Asp Lys Phe Ala Phe
        115                 120                 125
Asp Pro Tyr Cys Leu Xaa Gly Thr Val Glu Phe Gly Ile Pro Arg Cys
    130                 135                 140
Asn Ile Glu Ser Leu Lys Gly Gly Pro Glu Tyr Asn Ala Glu Val
145                 150                 155                 160
Leu Lys Arg Val Leu Gly Gly Glu Arg Gly Pro Ile Ala Asp Ala Leu
                165                 170                 175
Ile Leu Asn Ala Ala Ala Leu Leu Val Ser Gly Cys Val Ser Asn
            180                 185                 190
Leu Ala Glu Gly Val Ser Val Ala Arg Glu Thr Gln Gln Ser Gly Lys
        195                 200                 205
Ala Leu Lys Thr Leu Asn Leu Leu Lys Asp Val Ser Asn Asn Ile Lys
    210                 215                 220
Asp Glu Leu Gly Met Asp Ala
225                 230
```

<210> SEQ ID NO 5
<211> LENGTH: 1005
<212> TYPE: DNA
<213> ORGANISM: Triticum aestivum

<400> SEQUENCE: 5

```
gcacgaggtc aacatcgagt tgggacccga gggtattaaa cggtgcgtca atgaggtggg    60
tgttggtttc atgatgtctg caaattacca tccggcaatg aaaattgtca gacctgtgag   120
gaagaagctg aagataaaga cagttttcaa tatccttggt cctctgttga atccagcaag   180
ggtaccttat gctgttattg tgtttacca cgagaacata gttagcaaga tggccaaagc   240
agctcagaaa tttggtatgc agagagcatt ggttgttcat tcaaagggtc tggacgaaat   300
aagcccactt gggcctggat atattcttga tgtcactcca ggaaagattg aaaaaatgct   360
cttcgatcca ttggattttg gcattccgcg ctgcacatta ttagatctta aggaggcga    420
tcctgcgttc aacgcaaaag ttctccagga tgttctcgct ggacaaagag gctcaattgc   480
agatgctctt gttctgaacg ccgcggcgtc cctccttgtt agcggcaaag tcaaaactct   540
gcaagagggt gtcgcgctag cacaggagac gcagcgctcc ggagtggcca tcaacacgct   600
cgagtcgtgg ataaaggttt ccaatagctg ctgagaccgg ggttgcttgg cgagcagcag   660
agctctccgc aataagacgc aaggaatgat gccaaataag gattctttta gtccatccat   720
tctccatcat atatatgtct gctcttcttg ttcctttgt tcgtctttgt cacaagcgta    780
cgtagatgcc gcctggtctg gtttggtttg ttcatccagc aatgttgtag tgtagagaga   840
aaccccatgt ggacgagatt gtaaggttat ggacggaaca gaacaggcgc atgcatgctt   900
atcttgttgg ctaaggtgga ttggttgatc attttgatct cagtttgttg cgttgtgaga   960
cctggaaaga aagatctgga tcatgtcaaa aaaaaaaaaa aaaaa              1005
```

<210> SEQ ID NO 6
<211> LENGTH: 210
<212> TYPE: PRT

<213> ORGANISM: Triticum aestivum

<400> SEQUENCE: 6

```
His Glu Val Asn Ile Glu Leu Gly Pro Glu Gly Ile Lys Arg Cys Val
 1               5                  10                  15

Asn Glu Val Gly Val Gly Phe Met Met Ser Ala Asn Tyr His Pro Ala
            20                  25                  30

Met Lys Ile Val Arg Pro Val Arg Lys Leu Lys Ile Lys Thr Val
        35                  40                  45

Phe Asn Ile Leu Gly Pro Leu Leu Asn Pro Ala Arg Val Pro Tyr Ala
    50                  55                  60

Val Ile Gly Val Tyr His Glu Asn Ile Val Ser Lys Met Ala Lys Ala
 65                 70                  75                  80

Ala Gln Lys Phe Gly Met Gln Arg Ala Leu Val Val His Ser Lys Gly
            85                  90                  95

Leu Asp Glu Ile Ser Pro Leu Gly Pro Gly Tyr Ile Leu Asp Val Thr
        100                 105                 110

Pro Gly Lys Ile Glu Lys Met Leu Phe Asp Pro Leu Asp Phe Gly Ile
    115                 120                 125

Pro Arg Cys Thr Leu Leu Asp Leu Lys Gly Gly Asp Pro Ala Phe Asn
130                 135                 140

Ala Lys Val Leu Gln Asp Val Leu Ala Gly Gln Arg Gly Ser Ile Ala
145                 150                 155                 160

Asp Ala Leu Val Leu Asn Ala Ala Ser Leu Leu Val Ser Gly Lys
            165                 170                 175

Val Lys Thr Leu Gln Glu Gly Val Ala Leu Ala Gln Glu Thr Gln Arg
        180                 185                 190

Ser Gly Val Ala Ile Asn Thr Leu Glu Ser Trp Ile Lys Val Ser Asn
    195                 200                 205

Ser Cys
    210
```

<210> SEQ ID NO 7
<211> LENGTH: 454
<212> TYPE: DNA
<213> ORGANISM: Zea mays

<400> SEQUENCE: 7

```
gcacgagggt gaacgaggac aggttatagc tcaaaaggat gtaattgttg taggagaatc      60
tgcgctgttc actcctgatg atatctcgtt cgttcaaaac gctggggtca aagcggttct     120
cgtcggggaa tccctcatca agcaggagga tccagggaaa gcaatcgctg gcttttcgg     180
caaagatatc tcgcatgctg gtgctaccta gagacgacgc agaagagcaa cagaatacca     240
gaaacgctac tccggggttgc atcattttgt gtaggggaga aaatcgagcg ttgcaatcag     300
aaatccaccc tttcgcagag ttttgatcgg tcgttttgtt tacctgacct gccaacttcc     360
ccatgctgct attttttgt gaccgagcca tctcaataat tacagatttt agtgcacaag     420
atgtatatgt tcaaaaaaaa aaaaaaaaa aaaa                                  454
```

<210> SEQ ID NO 8
<211> LENGTH: 69
<212> TYPE: PRT
<213> ORGANISM: Zea mays

<400> SEQUENCE: 8

His Glu Gly Glu Arg Gly Gln Val Ile Ala Gln Lys Asp Val Ile Val

```
            1               5                  10                 15
Val Gly Glu Ser Ala Leu Phe Thr Pro Asp Asp Ile Ser Phe Val Gln
                    20                 25                 30

Asn Ala Gly Val Lys Ala Val Leu Val Gly Glu Ser Leu Ile Lys Gln
            35                 40                 45

Glu Asp Pro Gly Lys Ala Ile Ala Gly Leu Phe Gly Lys Asp Ile Ser
        50                 55                 60

His Ala Gly Ala Thr
 65
```

<210> SEQ ID NO 9
<211> LENGTH: 1437
<212> TYPE: DNA
<213> ORGANISM: Zea mays

<400> SEQUENCE: 9

| | | | | |
|---|---|---|---|---|
| gggaggagga | gacccaccgt | cggctcgccc | gtgtcccgat | tcccactcac gacatcaacc | 60 |
| tgtccccatc | catctcgccc | gcgacgtttg | atggagtctc | tcctcgcctc gcgatccatt | 120 |
| aggtcttcct | tctccgccgt | cgccagcacc | aggggcgccg | cttcccccag gccctcgcgc | 180 |
| gtcgccaccc | tcgccagcgc | cggcgccggc | gcccgctccc | gcgcgctccg tgctggccac | 240 |
| acggacgata | tgctgaacgc | aaaggagctg | gtccaatggg | agaatggctt gtcattcaat | 300 |
| gacatagcgg | ctaggcaggg | gattcgcatc | cgcagacact | gccgcccac tgcctccttg | 360 |
| aaggagatag | aggaggagct | gggagccccc | cttaacatcc | tagagaagat catttgggac | 420 |
| aaggagattg | aagtagctga | ggggcatgct | aagaagcctc | ttgaggaggt gattcaggct | 480 |
| gcaacgaaag | cccctccttc | aagagacttc | tatggcgctt | tagaagctgc ctacaagcgt | 540 |
| aatggggtgc | ctgcattgat | tgctgaggtc | aagaaagcat | ccccgagtag ggtgtgctc | 600 |
| agggagaact | ttaatcctgt | tgaaattgct | caagcttatg | aaaagaatgg agctgcatgt | 660 |
| ttgagcattt | tgacagatga | gaagtacttt | cagggaagct | ttgataatct tgaaaaggtg | 720 |
| cgcagctcag | gagtgaagtg | ccctcttctc | tgcaaggagt | ttgtcattga caagtggcaa | 780 |
| atctataatg | ctcgctctaa | gggtgctgat | gcaattctac | taattgctgc tgtgctacca | 840 |
| gatcttgaca | taaggaaatt | tcttcagatt | tgcgaagagt | tgggaatgac agctcttatt | 900 |
| gaggttcatg | atgaaagaga | gatggaacgt | gtgctgaaga | taaatggagt taagcttatt | 960 |
| ggtatcaata | accgaagcct | tgagacattt | gttgttgata | cttcgaacac caagatgttg | 1020 |
| ctcgagaaac | atggggatat | catcagggag | aagggaattt | tggttgttgg tgaatcaggt | 1080 |
| ctgtttactc | cggatgatgt | tgcttatgtt | cagaatgctg | gcgtttctgc tgttttggtt | 1140 |
| ggggaatccc | tggtgaagca | agagtgccct | ggacgagcca | ttgttgggtt atttggcaaa | 1200 |
| gaactgctgc | actgaatgag | aggacaaaga | ttgtagtagt | acatggtttg gtggtgaggt | 1260 |
| gttagtgcta | ggctgctagc | tgttagccat | agcatcattt | gcagtaatag cattggtttt | 1320 |
| attaataata | ccaccgaatg | tgacatgcag | aataaaaata | atgttcaata agttccattc | 1380 |
| aaaaaaaaa | aaaaaaaaa | aaaaaaaaa | aaaaaactc | gagggggcc cgtacac | 1437 |

<210> SEQ ID NO 10
<211> LENGTH: 374
<212> TYPE: PRT
<213> ORGANISM: Zea mays

<400> SEQUENCE: 10

Met Glu Ser Leu Leu Ala Ser Arg Ser Ile Arg Ser Ser Phe Ser Ala

```
             1               5              10              15
     Val Ala Ser Thr Arg Gly Ala Ala Ser Pro Arg Pro Ser Arg Val Ala
                    20                  25                  30

Thr Leu Ala Ser Ala Gly Ala Gly Ala Arg Ser Arg Ala Leu Arg Ala
                    35                  40                  45

Gly His Thr Asp Asp Met Leu Asn Ala Lys Glu Leu Val Gln Trp Glu
                    50                  55                  60

Asn Gly Leu Ser Phe Asn Asp Ile Ala Ala Arg Gln Gly Ile Arg Ile
      65                  70                  75                  80

Arg Arg His Cys Arg Pro Thr Ala Ser Leu Lys Glu Ile Glu Glu Glu
                    85                  90                  95

Leu Gly Ala Pro Leu Asn Ile Leu Glu Lys Ile Ile Trp Asp Lys Glu
                   100                 105                 110

Ile Glu Val Ala Glu Gly His Ala Lys Lys Pro Leu Glu Glu Val Ile
                   115                 120                 125

Gln Ala Ala Thr Lys Ala Pro Pro Ser Arg Asp Phe Tyr Gly Ala Leu
                   130                 135                 140

Glu Ala Ala Tyr Lys Arg Asn Gly Val Pro Ala Leu Ile Ala Glu Val
     145                 150                 155                 160

Lys Lys Ala Ser Pro Ser Arg Gly Val Leu Arg Glu Asn Phe Asn Pro
                   165                 170                 175

Val Glu Ile Ala Gln Ala Tyr Glu Lys Asn Gly Ala Ala Cys Leu Ser
                   180                 185                 190

Ile Leu Thr Asp Glu Lys Tyr Phe Gln Gly Ser Phe Asp Asn Leu Glu
                   195                 200                 205

Lys Val Arg Ser Ser Gly Val Lys Cys Pro Leu Leu Cys Lys Glu Phe
                   210                 215                 220

Val Ile Asp Lys Trp Gln Ile Tyr Asn Ala Arg Ser Lys Gly Ala Asp
     225                 230                 235                 240

Ala Ile Leu Leu Ile Ala Ala Val Leu Pro Asp Leu Asp Ile Arg Lys
                   245                 250                 255

Phe Leu Gln Ile Cys Glu Glu Leu Gly Met Thr Ala Leu Ile Glu Val
                   260                 265                 270

His Asp Glu Arg Glu Met Glu Arg Val Leu Lys Ile Asn Gly Val Lys
                   275                 280                 285

Leu Ile Gly Ile Asn Asn Arg Ser Leu Glu Thr Phe Val Asp Thr
                   290                 295                 300

Ser Asn Thr Lys Met Leu Leu Glu Lys His Gly Asp Ile Ile Arg Glu
     305                 310                 315                 320

Lys Gly Ile Leu Val Val Gly Glu Ser Gly Leu Phe Thr Pro Asp Asp
                   325                 330                 335

Val Ala Tyr Val Gln Asn Ala Gly Val Ser Ala Val Leu Val Gly Glu
                   340                 345                 350

Ser Leu Val Lys Gln Glu Cys Pro Gly Arg Ala Ile Val Gly Leu Phe
                   355                 360                 365

Gly Lys Glu Leu Leu His
         370

<210> SEQ ID NO 11
<211> LENGTH: 428
<212> TYPE: DNA
<213> ORGANISM: Oryza sativa

<400> SEQUENCE: 11
```

-continued

| | |
|---|---|
| gcacgagctt acatgtaagc tcgtgccggc acgagcttac atcgttgggg agtctctcat | 60 |
| caagcaggag gatcctggca aagcaatcgc tgggcttttc ggcaaagaca tctcacctgt | 120 |
| gagtgctgcg taaagtctaa agacaaacag agtggcagag aggctgagaa atgatggagc | 180 |
| acatcatcat attgtacagg gagagatgga gcaattagct tttctggaga gttttggtc | 240 |
| agccattttt tgtttactaa actcgatcag ttcttcccat atactcttgt gaccaaacct | 300 |
| tttcgaccaa tacaaatggt tcactgcaaa gaaatatatg atcgaataag ttggatttaa | 360 |
| ttgcaaggag tacgagttca tatttccttt ggaatatgga acatcaaaaa aaaaaaaaaa | 420 |
| aaaaaact | 428 |

<210> SEQ ID NO 12
<211> LENGTH: 43
<212> TYPE: PRT
<213> ORGANISM: Oryza sativa

<400> SEQUENCE: 12

His Glu Leu Thr Cys Lys Leu Val Pro Ala Arg Ala Tyr Ile Val Gly
 1               5                  10                  15
Glu Ser Leu Ile Lys Gln Glu Asp Pro Gly Lys Ala Ile Ala Gly Leu
            20                  25                  30
Phe Gly Lys Asp Ile Ser Pro Val Ser Ala Ala
            35                  40

<210> SEQ ID NO 13
<211> LENGTH: 1624
<212> TYPE: DNA
<213> ORGANISM: Glycine max

<400> SEQUENCE: 13

| | |
|---|---|
| cggtttccct ctagaaataa ttttgtttaa ctttaagaag agatatacc atgggcagca | 60 |
| gccatcatca tcatcatcac agcagcggcc tggtgccgcg cggcagccat atggaaggtt | 120 |
| tggcttccct caaggctccc tttccggcca ccccatttct ctcttccaga cccagaacct | 180 |
| ctattcttcc atcccaagcc agttttcgta aagaagctc cttttatcc ttttctgttc | 240 |
| atgcccaggt ggagtctgat gatggttcag ctgtagtagc cacatctggt gaatctgtga | 300 |
| cagaggttct gaaaattaag gagtgggagg tgggaatgtt ccaaaatgag gttgcagcta | 360 |
| gccagggtat aagaataagg agaaggcctc catctggacc cccttttgcat tatgtaggac | 420 |
| catttcaatt caggttgcag aatgagggca atacgccccg gaacattttg aagagattg | 480 |
| tgtggaataa ggacacagaa gtctcacagc ttaaagaaag aaaacccctt ggcgtgctga | 540 |
| agaaagctct tgaaaatgca cctcctgcta gggattttat tggtgctcta aaggcagcca | 600 |
| acgaacgaac tggacttcca gggttgattg ctgaagtgaa gaaggcatca ccaagtagag | 660 |
| gtatcttgag agaagacttt gacccagttg aaattgctaa ggcttatgag aaaggtggag | 720 |
| cagcatgtct aagtgttttg acagatgaaa agtattttaa gggaagcttt gaaaatcttg | 780 |
| aggcaataag aaaggctggc ataaagtgcc ctttgttgtg caaagaattc atcatagatg | 840 |
| catggcaact ctactatgct cgaactaaag gtgcagatgc agtcctttta attgctgctg | 900 |
| ttttgcctga tcttgacatc aaatacatga ttaagatatg caaattactc ggattgactg | 960 |
| cgcttgttga ggttcatgat gagagggaat tgatcgtgt tcttgcaata gagggggattg | 1020 |
| agcttattgg cattaacaac cgcaatcttg aacatttga gttggatatc agcatcacaa | 1080 |
| agaaacttct tgaaggagag cgaggcaaaa taatccacga gagaggcata attatggttg | 1140 |

-continued

```
gggaatctgg tctctttacc ccggacgata ttgcctatgt tcaggaagct ggtgttaaag   1200
ctatattggt tggagagtct attgtaaaac aaagtgatcc tggaaaggga atcagcaatc   1260
tctttggcaa agatatctct ttgggttgaa gtgagctata tttcttgaga tataagcttt   1320
tgagatgaca gattttgctc aggttaatga tttgatacct tcgacctttg cttgtaccaa   1380
attatcaaaa tcttaccagt agcaaatatg taccaaaata aactcttatt gtttaataat   1440
actttgcaac taaatgatat cattttgaga taatagtttg cgacaaaaa aaaaaaaaa    1500 aaactcgagg ggggcccgg tacccaattc gccctatgga tccgagctcg agatctgcag   1560
ctggtaccat ggaattcgaa gcttgatccg gctgctaaca agcccgaaa ggaaggtgag   1620 ttgc                                                               1624
```

<210> SEQ ID NO 14
<211> LENGTH: 392
<212> TYPE: PRT
<213> ORGANISM: Glycine max

<400> SEQUENCE: 14

```
Met Glu Gly Leu Ala Ser Leu Lys Ala Pro Phe Pro Ala Thr Pro Phe
  1               5                  10                  15

Leu Ser Ser Arg Pro Arg Thr Ser Ile Leu Pro Ser Gln Ala Ser Phe
                 20                  25                  30

Arg Lys Arg Ser Ser Phe Leu Ser Phe Ser Val His Ala Gln Val Glu
             35                  40                  45

Ser Asp Asp Gly Ser Ala Val Ala Thr Ser Gly Glu Ser Val Thr
         50                  55                  60

Glu Val Leu Lys Ile Lys Glu Trp Glu Val Gly Met Phe Gln Asn Glu
 65                  70                  75                  80

Val Ala Ala Ser Gln Gly Ile Arg Ile Arg Arg Pro Ser Gly
                 85                  90                  95

Pro Pro Leu His Tyr Val Gly Pro Phe Gln Phe Arg Leu Gln Asn Glu
                100                 105                 110

Gly Asn Thr Pro Arg Asn Ile Leu Glu Glu Ile Val Trp Asn Lys Asp
            115                 120                 125

Thr Glu Val Ser Gln Leu Lys Glu Arg Lys Pro Leu Gly Val Leu Lys
        130                 135                 140

Lys Ala Leu Glu Asn Ala Pro Pro Ala Arg Asp Phe Ile Gly Ala Leu
145                 150                 155                 160

Lys Ala Ala Asn Glu Arg Thr Gly Leu Pro Gly Leu Ile Ala Glu Val
                165                 170                 175

Lys Lys Ala Ser Pro Ser Arg Gly Ile Leu Arg Glu Asp Phe Asp Pro
            180                 185                 190

Val Glu Ile Ala Lys Ala Tyr Glu Lys Gly Gly Ala Ala Cys Leu Ser
        195                 200                 205

Val Leu Thr Asp Glu Lys Tyr Phe Lys Gly Ser Phe Glu Asn Leu Glu
    210                 215                 220

Ala Ile Arg Lys Ala Gly Ile Lys Cys Pro Leu Leu Cys Lys Glu Phe
225                 230                 235                 240

Ile Ile Asp Ala Trp Gln Leu Tyr Tyr Ala Arg Thr Lys Gly Ala Asp
                245                 250                 255

Ala Val Leu Leu Ile Ala Ala Val Leu Pro Asp Leu Asp Ile Lys Tyr
            260                 265                 270

Met Ile Lys Ile Cys Lys Leu Leu Gly Leu Thr Ala Leu Val Glu Val
        275                 280                 285
```

```
His Asp Glu Arg Glu Phe Asp Arg Val Leu Ala Ile Glu Gly Ile Glu
    290                 295                 300
Leu Ile Gly Ile Asn Asn Arg Asn Leu Glu Thr Phe Glu Leu Asp Ile
305                 310                 315                 320
Ser Ile Thr Lys Lys Leu Leu Glu Gly Glu Arg Gly Lys Ile Ile His
                325                 330                 335
Glu Arg Gly Ile Ile Met Val Gly Glu Ser Gly Leu Phe Thr Pro Asp
            340                 345                 350
Asp Ile Ala Tyr Val Gln Glu Ala Gly Val Lys Ala Ile Leu Val Gly
        355                 360                 365
Glu Ser Ile Val Lys Gln Ser Asp Pro Gly Lys Gly Ile Ser Asn Leu
    370                 375                 380
Phe Gly Lys Asp Ile Ser Leu Gly
385                 390
```

<210> SEQ ID NO 15
<211> LENGTH: 1005
<212> TYPE: DNA
<213> ORGANISM: Triticum aestivum

<400> SEQUENCE: 15

| | | | | | |
|---|---|---|---|---|---|
| aagatcatct | gggacaagga | gatcgaagtg | gcccagggc | ttgccagaaa | tcctctgaat | 60 |
| gaggtgattg | agtctgcagg | gaaggctcct | cctacaagag | acttctatgg | tgctttggca | 120 |
| gcagcccaca | agcgtaatgg | ggtgccagca | ttgatcgctg | aggtcaagaa | ggcgtcacca | 180 |
| agtagggggcg | tactcaggga | gaactttgat | cctgttgaaa | ttgctcaagc | ttatgaaaag | 240 |
| catggagctg | catgcttgag | catcttgact | gatgagaaat | acttccaggg | aagtttcgag | 300 |
| aatcttcaga | aggtgcgcaa | agcaggagtt | aagtgccccc | ttctgtgcaa | agagttcgtc | 360 |
| gttgacaaat | ggcagatcta | ttatgcccgt | actatgggtg | ctgatgcagt | tctgctaatt | 420 |
| gctgctgtgc | taactgatct | cgacataaaa | tacttccttc | gaatatgcaa | ggagttggga | 480 |
| ttgacggctc | ttattgaggt | tcatgatgaa | agagagatgg | agcgtatcct | tgcgataaat | 540 |
| ggtgttcagc | ttattggcat | caacaaccgt | agtcttgaga | catttatagt | ggatacttcg | 600 |
| aacacgaaga | cgttgctgga | gaagcatggc | aatgccatca | gggagaaggg | aatattggtt | 660 |
| gttggagaat | cagggctatt | cacccccagat | gatgttgctt | atgtgcagaa | tgctggagtc | 720 |
| tccgctgttt | tggtaggcga | atccttggtg | aagcaagcgg | accctgggcg | agccatcgct | 780 |
| gggctcttcg | gaagagaact | ggtgcactga | acaactaga | ccagacttgt | tgtggtagaa | 840 |
| ctagtagtag | tagctgccag | accaccgcat | gatgaataat | aatggtctcc | ttttcttttg | 900 |
| gctgagcaac | aagatttgat | cttttttatg | cgggaaataa | acatattctt | tatttatggg | 960 |
| gaataaattt | atgatctacc | aaaaaaaaaa | aaaaaaaaac | tcgag |  | 1005 |

<210> SEQ ID NO 16
<211> LENGTH: 269
<212> TYPE: PRT
<213> ORGANISM: Triticum aestivum

<400> SEQUENCE: 16

```
Lys Ile Ile Trp Asp Lys Glu Ile Glu Val Ala Gln Gly Leu Ala Arg
  1               5                  10                  15
Asn Pro Leu Asn Glu Val Ile Glu Ser Ala Gly Lys Ala Pro Pro Thr
             20                  25                  30
Arg Asp Phe Tyr Gly Ala Leu Ala Ala Ala His Lys Arg Asn Gly Val
```

```
                    35                  40                  45
Pro Ala Leu Ile Ala Glu Val Lys Lys Ala Ser Pro Ser Arg Gly Val
 50                  55                  60

Leu Arg Glu Asn Phe Asp Pro Val Glu Ile Ala Gln Ala Tyr Glu Lys
 65                  70                  75                  80

His Gly Ala Ala Cys Leu Ser Ile Leu Thr Asp Glu Lys Tyr Phe Gln
                 85                  90                  95

Gly Ser Phe Glu Asn Leu Gln Lys Val Arg Lys Ala Gly Val Lys Cys
            100                 105                 110

Pro Leu Leu Cys Lys Glu Phe Val Val Asp Lys Trp Gln Ile Tyr Tyr
        115                 120                 125

Ala Arg Thr Met Gly Ala Asp Ala Val Leu Leu Ile Ala Ala Val Leu
130                 135                 140

Thr Asp Leu Asp Ile Lys Tyr Phe Leu Arg Ile Cys Lys Glu Leu Gly
145                 150                 155                 160

Leu Thr Ala Leu Ile Glu Val His Asp Glu Arg Glu Met Glu Arg Ile
                165                 170                 175

Leu Ala Ile Asn Gly Val Gln Leu Ile Gly Ile Asn Asn Arg Ser Leu
            180                 185                 190

Glu Thr Phe Ile Val Asp Thr Ser Asn Thr Lys Thr Leu Leu Glu Lys
        195                 200                 205

His Gly Asn Ala Ile Arg Glu Lys Gly Ile Leu Val Val Gly Glu Ser
210                 215                 220

Gly Leu Phe Thr Pro Asp Asp Val Ala Tyr Val Gln Asn Ala Gly Val
225                 230                 235                 240

Ser Ala Val Leu Val Gly Glu Ser Leu Val Lys Gln Ala Asp Pro Gly
                245                 250                 255

Arg Ala Ile Ala Gly Leu Phe Gly Arg Glu Leu Val His
            260                 265

<210> SEQ ID NO 17
<211> LENGTH: 685
<212> TYPE: DNA
<213> ORGANISM: Zea mays
<220> FEATURE:
<221> NAME/KEY: unsure
<222> LOCATION: (307)
<223> OTHER INFORMATION: n = a, c, t, or g
<220> FEATURE:
<221> NAME/KEY: unsure
<222> LOCATION: (672)
<223> OTHER INFORMATION: n = a, c, t, or g

<400> SEQUENCE: 17
tgctgctcta gcccacctgc atggcggtgt cagcgccggt cactctctgc ccctcggatt      60
ctcgctccct ctcttccgcg ctcgtttctt cccgatccaa caagccttcc tcacttgatg    120
ctgttcggtc acggcggttg aatttgggag attcagctat gccaacgcag atctccacaa    180
ggcactctct tcggtttgct ttaccttcga acaatgcacg tccaatatcg actgcagcaa    240
gaatggcatg ttttgctaag aagcaacctg ttgctgccgt gcccttatgt actttggagg    300
ccaaaanata tgaacctata gtcaaaatgt gtggcattac atctgccttc gatgctgaga    360
tggctttgaa ggctggagct aaattaattg ggatgattct ttggcccaag tccaaacgct    420
ctatcccatt gtctgaagct aaagagatat ccagagtggc caaatcttac ggggctgaat    480
cagtgggtgt gtttgtggat gatgatagta gtactatctt gacagcatct gattcatgca    540
acctcgatct tatccagctt catggagata gctcccgaga actacttcct ctgctttgga    600
```

```
aagaacaaca ggatatatat gtgctaaaat gctgatgagg atggtaaact tatcaatgct      660
cctccaagtg angaatatgt tcctt                                           685
```

<210> SEQ ID NO 18
<211> LENGTH: 158
<212> TYPE: PRT
<213> ORGANISM: Zea mays
<220> FEATURE:
<221> NAME/KEY: UNSURE
<222> LOCATION: (50)
<223> OTHER INFORMATION: XAA = ANY AMINO ACID

<400> SEQUENCE: 18

```
Met Pro Thr Gln Ile Ser Thr Arg His Ser Leu Arg Phe Ala Leu Pro
 1               5                  10                  15

Ser Asn Asn Ala Arg Pro Ile Ser Thr Ala Ala Arg Met Ala Cys Phe
            20                  25                  30

Ala Lys Lys Gln Pro Val Ala Ala Val Pro Leu Cys Thr Leu Glu Ala
        35                  40                  45

Lys Xaa Tyr Glu Pro Ile Val Lys Met Cys Gly Ile Thr Ser Ala Phe
    50                  55                  60

Asp Ala Glu Met Ala Leu Lys Ala Gly Ala Lys Leu Ile Gly Met Ile
65                  70                  75                  80

Leu Trp Pro Lys Ser Lys Arg Ser Ile Pro Leu Ser Glu Ala Lys Glu
                85                  90                  95

Ile Ser Arg Val Ala Lys Ser Tyr Gly Ala Glu Ser Val Gly Val Phe
            100                 105                 110

Val Asp Asp Asp Ser Ser Thr Ile Leu Thr Ala Ser Asp Ser Cys Asn
        115                 120                 125

Leu Asp Leu Ile Gln Leu His Gly Asp Ser Ser Arg Glu Leu Leu Pro
    130                 135                 140

Leu Leu Trp Lys Glu Gln Gln Asp Ile Tyr Val Leu Lys Cys
145                 150                 155
```

<210> SEQ ID NO 19
<211> LENGTH: 1292
<212> TYPE: DNA
<213> ORGANISM: Zea mays

<400> SEQUENCE: 19

```
gcacgagctc tctctcgtag tcgtgcggcc accgggtgac tgccggcgcc gccctaagcc      60
aggtgccgtc ttcgttgggt ccctcggttg cgacgagcac ccaccagtaa tgctgttggc     120
aagctcaaca agacgctatg agcaatttcc tttagcacga acaatggacc ttccaagatt     180
ttcaagagta aaaatgtcat gcttgggaac aaaccaaagt aaccatcatt ctgataccgt     240
cagatcttca tccctagtt gtggagatac cagaaaggtc caccctgtag tcaaaatgtg      300
tggcatcaca tcagctagag atgcagaaat ggctgtaaaa gcaggagctg agcttatagg     360
catgatacta tggcccaact ctaaacgctc tgtctcgtta ttggaggcaa agaaatatc      420 aagagttgtg caatcttatg gcgctgaatc agttggtgtc tttgtggatg ataatgaaga     480
gacaattcta cgagtgtctg attcatgtga ccttaacttt gtccagcttc atggtgatga     540
atctcgtgca ttggttcata ctctttcaaa gaataatcgt atcgtttatg tactaaatgc     600
tgatgacgat ggaaaactaa tcaacattcc tgatattgaa tacgaacttg attggtactt     660
agtggacagt gcaaagggcg gaagtggaaa gggattcaac tggcagaagt tccagatgcc     720
```

```
atctgtcaaa agcaagaatg gatggctatt agctggaggg cttcatgcag ataatgtttg     780
tgaagccttt tctgctctga aaccagatgg tgttgatgtt agcagcggca tatgtggtcg     840
agatggtatc cgaaaagatg cagacaggat taattccttc ataagtaatg tgaaatccct     900
aaattttcta tcgtaaggtc atttgcttgt cgagagctta gttttatttc atttgctcac     960
gtgtggaatc cctgaattgc tgcaacctga aggcaagctg tcaaaattgc tcttggggct    1020
gagggcaaaa gagtgattga attttgaag tgtgaacata tgtatccggt ttattgtgga    1080
gtgtggcaaa ctcgttactg caacctgaag gcaagatgtt caaattgcgc ttgagaatag    1140
ggattacatt tttgaatgtg agtattgtgt ttgtttctag tgcaataagt gtgttttgta    1200
tgcatgtcca gttcaaatgc aaaaataaaa acacattgta ccgttgacaa aattgctgca    1260
gtaaaagctg gagaatttt attaaaaaaa aa                                   1292
```

<210> SEQ ID NO 20
<211> LENGTH: 268
<212> TYPE: PRT
<213> ORGANISM: Zea mays

<400> SEQUENCE: 20

```
Met Leu Leu Ala Ser Ser Thr Arg Arg Tyr Glu Gln Phe Pro Leu Ala
 1               5                  10                  15

Arg Asn Asn Gly Leu Pro Arg Phe Ser Arg Val Lys Met Ser Cys Leu
            20                  25                  30

Gly Thr Asn Gln Ser Asn His His Ser Asp Thr Val Arg Ser Ser Ser
        35                  40                  45

Pro Ser Cys Gly Asp Thr Arg Lys Val His Pro Val Lys Met Cys
    50                  55                  60

Gly Ile Thr Ser Ala Arg Asp Ala Glu Met Ala Val Lys Ala Gly Ala
 65                  70                  75                  80

Glu Leu Ile Gly Met Ile Leu Trp Pro Asn Ser Lys Arg Ser Val Ser
                85                  90                  95

Leu Leu Glu Ala Lys Glu Ile Ser Arg Val Val Gln Ser Tyr Gly Ala
            100                 105                 110

Glu Ser Val Gly Val Phe Val Asp Asp Asn Glu Glu Thr Ile Leu Arg
        115                 120                 125

Val Ser Asp Ser Cys Asp Leu Asn Phe Val Gln Leu His Gly Asp Glu
    130                 135                 140

Ser Arg Ala Leu Val His Thr Leu Ser Lys Asn Asn Arg Ile Val Tyr
145                 150                 155                 160

Val Leu Asn Ala Asp Asp Asp Gly Lys Leu Ile Asn Ile Pro Asp Ile
                165                 170                 175

Glu Tyr Glu Leu Asp Trp Tyr Leu Val Asp Ser Ala Lys Gly Gly Ser
            180                 185                 190

Gly Lys Gly Phe Asn Trp Gln Lys Phe Gln Met Pro Ser Val Lys Ser
        195                 200                 205

Lys Asn Gly Trp Leu Leu Ala Gly Gly Leu His Ala Asp Asn Val Cys
    210                 215                 220

Glu Ala Phe Ser Ala Leu Lys Pro Asp Gly Val Asp Val Ser Ser Gly
225                 230                 235                 240

Ile Cys Gly Arg Asp Gly Ile Arg Lys Asp Ala Asp Arg Ile Asn Ser
                245                 250                 255

Phe Ile Ser Asn Val Lys Ser Leu Asn Phe Leu Ser
            260                 265
```

```
<210> SEQ ID NO 21
<211> LENGTH: 551
<212> TYPE: DNA
<213> ORGANISM: Oryza sativa
<220> FEATURE:
<221> NAME/KEY: unsure
<222> LOCATION: (414)
<223> OTHER INFORMATION: n = a, c, t, or g
<220> FEATURE:
<221> NAME/KEY: unsure
<222> LOCATION: (445)
<223> OTHER INFORMATION: n = a, c, t, or g
<220> FEATURE:
<221> NAME/KEY: unsure
<222> LOCATION: (464)
<223> OTHER INFORMATION: n = a, c, t, or g
<220> FEATURE:
<221> NAME/KEY: unsure
<222> LOCATION: (494)
<223> OTHER INFORMATION: n = a, c, t, or g
<220> FEATURE:
<221> NAME/KEY: unsure
<222> LOCATION: (508)
<223> OTHER INFORMATION: n = a, c, t, or g
<220> FEATURE:
<221> NAME/KEY: unsure
<222> LOCATION: (522)
<223> OTHER INFORMATION: n = a, c, t, or g
<220> FEATURE:
<221> NAME/KEY: unsure
<222> LOCATION: (549)
<223> OTHER INFORMATION: n = a, c, t, or g

<400> SEQUENCE: 21
gttctaacgt gaccttaatc tagtgcagct tcatggagat gaatctcgtt cattacttca      60
tgtgctatcg aagaacaatc gcatcattta tgttctaaat gccaatgacg acggaaagct     120
tatcaacgct cttcctgatg aaaaatatga gcttgattgg ttcttggtgg atagtgccaa     180
aggtggaagt ggcaagggat tcaactggca gaagtttcag atgccgtctg ttcgaagcaa     240
gaatgggtgg cttttagctg gaggccttca cgctgataat gtttgtgatg ccttttatgc     300
cctgaaacca aatggagtgg atgttagcag tggaatatgt gctcctgatg gtatcagaaa     360
agatcccacg aggatttctt ctttcatgag aaatgttaaa tccttgggca gatnacaatg     420
attattctgg tgtttggagg gtaanctcaa tttggttgcc taangtggag aatgaacaaa     480
atctcctctg aaanaaactg gtcaattnat ccacaaggga angggaaat gccattgggg     540 ttaaagccna a                                                         551

<210> SEQ ID NO 22
<211> LENGTH: 136
<212> TYPE: PRT
<213> ORGANISM: Oryza sativa
<220> FEATURE:
<221> NAME/KEY: UNSURE
<222> LOCATION: (135)
<223> OTHER INFORMATION: XAA = ANY AMINO ACID

<400> SEQUENCE: 22
```

Asp Leu Asn Leu Val Gln Leu His Gly Asp Glu Ser Arg Ser Leu Leu
 1               5                  10                  15

His Val Leu Ser Lys Asn Asn Arg Ile Ile Tyr Val Leu Asn Ala Asn
            20                  25                  30

Asp Asp Gly Lys Leu Ile Asn Ala Leu Pro Asp Glu Lys Tyr Glu Leu
        35                  40                  45

Asp Trp Phe Leu Val Asp Ser Ala Lys Gly Gly Ser Gly Lys Gly Phe
    50                  55                  60

```
Asn Trp Gln Lys Phe Gln Met Pro Ser Val Arg Ser Lys Asn Gly Trp
 65                  70                  75                  80

Leu Leu Ala Gly Gly Leu His Ala Asp Asn Val Cys Asp Ala Phe Tyr
                 85                  90                  95

Ala Leu Lys Pro Asn Gly Val Asp Val Ser Ser Gly Ile Cys Ala Pro
            100                 105                 110

Asp Gly Ile Arg Lys Asp Pro Thr Arg Ile Ser Ser Phe Met Arg Asn
        115                 120                 125

Val Lys Ser Leu Gly Arg Xaa Gln
    130                 135

<210> SEQ ID NO 23
<211> LENGTH: 1113
<212> TYPE: DNA
<213> ORGANISM: Triticum aestivum

<400> SEQUENCE: 23
gcacgagcac cgggccgctc tgttccttcc ttcctcatcc tcttttcccc gtttcgtcgc    60
tcgtccacgc cgtggagaga ccgcagacca gagccgttcg caccgccatt gcagcttgcc   120
cagccaggtg ctcgagcgtt cctgctcgcc cgcggctcct ggcctcctc agcagcgatg   180
gcgacagcgt tctcaacgaa gcagccgctg cgggtcgcta cgcctacaaa caatggcgt   240
ccaaggttgc cgctaattaa aatgcaatat tcgtccaaca aacgagccag tgcttccatt   300
tcattgccat ccagtgccga gggtgtggag agaaacgagc ccatagtcaa atgtgtggc   360
atcacatctg ctagagatgc agaattcgct gcaaaggctg gagctaaact tatcgggatg   420
attctttggc ccaagtccaa acgatctgtc aacggtcag aagcgaagga atatccaga    480
gtagcaaagt catatggggc tgaagctgtt ggtgtgtttg tcgatgatga cgaagagacc   540
atcttaagag tagccgattc atgcaacctt caacttattc agcttcatgg agatagttct   600
cgggcactag ttcctgctct tgccaagaac aaccgaattg tgtatgttct taatgctgac   660
gcggacggaa aacttatcaa ttccccccc agtgaagaat acgacattga ctggtttttg   720
gtggacagtg cagagggtgg aagcggcaaa ggattcaact gggacaattt tcgaatgcca   780
tcggtgaaaa gcaagaacgg ctggctgcta gcaggaggcc ttcatgcgga caatgtttgc   840
caagctgctt ccgctctaaa accaaatggt gtggatgtta gcagtggaat atgctctcct   900
gacggtataa gcaaggaccc gaagaggata tcgtccttca tgagaagcgt gcaatcctta   960
agttcccgac gaggtctcta tttagacgcc ccaggctttat tgtagcttct tgcttcagtt  1020
tgtgaagaca tttgcaaata agctgtcctg aatgatagca gtaaataaac aactttgaag  1080
cggagttcca actaaaaaaa aaaaaaaaa aaa                                 1113

<210> SEQ ID NO 24
<211> LENGTH: 275
<212> TYPE: PRT
<213> ORGANISM: Triticum aestivum

<400> SEQUENCE: 24

Met Ala Thr Ala Phe Ser Thr Lys Gln Pro Leu Arg Val Ala Thr Pro
  1               5                  10                  15

Thr Asn Lys Trp Arg Pro Arg Leu Pro Leu Ile Lys Met Gln Tyr Ser
             20                  25                  30

Ser Asn Lys Arg Ala Ser Ala Ser Ile Ser Leu Pro Ser Ser Ala Glu
         35                  40                  45
```

```
Gly Val Glu Arg Asn Glu Pro Ile Val Lys Met Cys Gly Ile Thr Ser
 50                  55                  60

Ala Arg Asp Ala Glu Phe Ala Ala Lys Ala Gly Ala Lys Leu Ile Gly
 65                  70                  75                  80

Met Ile Leu Trp Pro Lys Ser Lys Arg Ser Val Gln Arg Ser Glu Ala
                 85                  90                  95

Lys Glu Ile Ser Arg Val Ala Lys Ser Tyr Gly Ala Glu Ala Val Gly
                100                 105                 110

Val Phe Val Asp Asp Glu Glu Thr Ile Leu Arg Val Ala Asp Ser
        115                 120                 125

Cys Asn Leu Gln Leu Ile Gln Leu His Gly Asp Ser Ser Arg Ala Leu
    130                 135                 140

Val Pro Ala Leu Ala Lys Asn Asn Arg Ile Val Tyr Val Leu Asn Ala
145                 150                 155                 160

Asp Ala Asp Gly Lys Leu Ile Asn Ser Pro Ser Glu Glu Tyr Asp
                165                 170                 175

Ile Asp Trp Phe Leu Val Asp Ser Ala Glu Gly Ser Gly Lys Gly
                180                 185                 190

Phe Asn Trp Asp Asn Phe Arg Met Pro Ser Val Lys Ser Lys Asn Gly
                195                 200                 205

Trp Leu Leu Ala Gly Gly Leu His Ala Asp Asn Val Cys Gln Ala Ala
210                 215                 220

Ser Ala Leu Lys Pro Asn Gly Val Asp Val Ser Ser Gly Ile Cys Ser
225                 230                 235                 240

Pro Asp Gly Ile Ser Lys Asp Pro Lys Arg Ile Ser Ser Phe Met Arg
                245                 250                 255

Ser Val Gln Ser Leu Ser Ser Arg Gly Leu Tyr Leu Asp Ala Pro
                260                 265                 270

Gly Leu Leu
        275

<210> SEQ ID NO 25
<211> LENGTH: 368
<212> TYPE: PRT
<213> ORGANISM: Arabidopsis thaliana

<400> SEQUENCE: 25

Met Asp Arg Lys Ile Asn Phe Arg Ala Pro Ser Gln Phe Ser Ile Arg
  1               5                  10                  15

Ala Gln Gln Ser Asp Leu Lys Glu Ser Leu Ala Val Ser Ser Ser
                 20                  25                  30

Val Glu Asp Lys Gly Asn Val Leu Arg Ile Lys Glu Trp Glu Val Glu
             35                  40                  45

Met Tyr Gln Glu Glu Leu Ala Ile Ser Gln Gly Ile Arg Ile Arg Arg
 50                  55                  60

Lys Pro Pro Ser Lys Ala Pro Leu Gly Tyr Ser Gly Pro Phe Glu Leu
 65                  70                  75                  80

Arg Leu His Asn Asn Asp Ala Asp Ser Pro Arg Asn Ile Leu Glu Glu
                 85                  90                  95

Ile Thr Trp Tyr Lys Asp Val Glu Val Ser Arg Met Lys Glu Leu Asn
                100                 105                 110

Pro Leu Asp Val Leu Lys Lys Ala Val Glu Asp Ala Pro Pro Thr Arg
            115                 120                 125

Asp Phe Val Gly Ala Leu Arg Met Ala His Lys Arg Pro Gly Phe Pro
            130                 135                 140
```

```
Gly Leu Ile Ala Glu Val Lys Lys Ala Ser Pro Ser Arg Gly Ile Leu
145                 150                 155                 160

Lys Glu Asn Phe Asp Pro Val Glu Ile Ala Gln Ala Tyr Glu Lys Gly
                165                 170                 175

Gly Ala Ala Cys Leu Ser Val Leu Thr Asp Gln Lys Tyr Phe Gln Gly
            180                 185                 190

Gly Phe Glu Asn Leu Glu Ala Ile Arg Ser Ala Gly Val Lys Cys Pro
        195                 200                 205

Leu Leu Cys Lys Glu Phe Val Val Asp Pro Trp Gln Ile Tyr Tyr Ala
    210                 215                 220

Arg Thr Lys Gly Ala Asp Ala Val Leu Leu Ile Ala Ala Val Leu Ala
225                 230                 235                 240

Asp Leu Glu Ile Thr Phe Leu Leu Lys Ile Cys Lys Lys Leu Ser Leu
                245                 250                 255

Ala Ala Leu Val Glu Val His Asp Glu Arg Glu Met Gly Arg Val Leu
            260                 265                 270

Gly Ile Glu Gly Ile Glu Leu Val Gly Ile Asn Asn Arg Ser Leu Glu
        275                 280                 285

Thr Phe Glu Val Asp Ile Ser Asn Thr Lys Lys Leu Leu Ala Leu Glu
    290                 295                 300

Gly Glu His Gly Arg Gln Ile Arg Glu Arg Asp Met Ile Val Val Gly
305                 310                 315                 320

Glu Ser Gly Leu Phe Thr Pro Asp Asp Ile Ala Tyr Val Gln Ala Ala
                325                 330                 335

Gly Val Lys Ala Val Leu Val Gly Glu Ser Ile Val Lys Gln Asn Asp
            340                 345                 350

Pro Glu Lys Gly Ile Ala Gly Leu Phe Gly Arg Asn Ile Ser His Thr
        355                 360                 365

<210> SEQ ID NO 26
<211> LENGTH: 275
<212> TYPE: PRT
<213> ORGANISM: Arabidopsis thaliana

<400> SEQUENCE: 26

Met Ser Thr Gly Ile Ser Ser Asp Leu His Leu His Pro Arg Ala Leu
1               5                   10                  15

Asn Phe Ser Lys Thr Ser Lys Ser Gly Leu Ser Asn Arg Lys Val Ser
                20                  25                  30

Phe Ser Ser Val Gly Tyr Ala Gln Asn Arg Lys Leu Ser Cys Ser Val
            35                  40                  45

Ser Ser Thr Glu Asn Val Ala Pro Lys Asp Asp Arg Gly Lys Asp
        50                  55                  60

Arg Pro Leu Val Lys Met Cys Gly Ile Thr Ser Ala Arg Asp Ala Ala
65                  70                  75                  80

Met Ala Val Glu Ala Gly Ala Asp Phe Ile Gly Met Ile Ile Trp Pro
                85                  90                  95

His Ser Lys Arg Ser Ile Ser Leu Ser Val Ala Lys Asp Ile Ser Gln
                100                 105                 110

Val Ala Arg Glu Gly Gly Ala Lys Pro Val Gly Val Phe Val Glu Asp
            115                 120                 125

Asp Glu Asn Thr Ile Leu Arg Ala Ala Asp Ser Ser Asp Leu Glu Leu
        130                 135                 140

Val Gln Leu His Gly Asn Ser Ser Arg Ala Ala Phe Ser Arg Leu Val
```

```
                145                 150                 155                 160
Arg Glu Arg Lys Val Ile Tyr Val Leu Asn Ala Asn Glu Asp Gly Lys
                165                 170                 175

Leu Leu Asn Val Val Pro Glu Glu Asp Gly His Leu Ala Asp Trp Ile
            180                 185                 190

Leu Val Asp Ser Ala Thr Gly Gly Ser Gly Lys Gly Phe Asn Trp Ala
        195                 200                 205

Gln Phe Lys Leu Pro Ser Val Arg Ser Arg Asn Gly Trp Leu Leu Ala
    210                 215                 220

Gly Gly Ile Asn Pro Thr Asn Val Ser Glu Ala Leu Ser Ile Leu Gln
225                 230                 235                 240

Pro Asp Gly Ile Asp Val Ser Ser Gly Ile Cys Gly Ile Asp Gly Ile
                245                 250                 255

Gln Lys Asp Lys Ser Lys Ile Ser Ser Phe Ile Thr Ala Val Arg Ser
            260                 265                 270

Val His Tyr
        275

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 27
tatggaaggt ttggcttccc tc                                              22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 28
tggaaggttt ggcttccctc                                                 20

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 29
tatggttctg aaaattaagg agtgg                                           25

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:PCR primer

<400> SEQUENCE: 30
tggttctgaa aattaaggag tgg                                             23

<210> SEQ ID NO 31
<211> LENGTH: 26
<212> TYPE: DNA
<213> ORGANISM: Artificial Sequence
```

```
<220> FEATURE:
<223> OTHER INFORMATION: Description of Artificial Sequence:PCR primer

<400> SEQUENCE: 31
gatccatagg ggcaattggg taccgg                                          26

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 32 catagggca attgggtacc gg                                               22
```